United States Patent
Soori-Arachi

(10) Patent No.: US 12,380,735 B2
(45) Date of Patent: Aug. 5, 2025

(54) SYSTEMS AND METHODS FOR BIOMETRIC IDENTIFICATION USING PATTERNS AND BLOOD FLOW CHARACTERISTICS OF THE OUTER EYE

(71) Applicant: O/D Vision Inc., Sanibel, FL (US)

(72) Inventor: Marcus Charles Bernard Soori-Arachi, Fort Myers, FL (US)

(73) Assignee: O/D Vision Inc., Sanibel, FL (US)

( * ) Notice: Subject to any disclaimer, the term of this patent is extended or adjusted under 35 U.S.C. 154(b) by 0 days.

(21) Appl. No.: 18/409,744

(22) Filed: Jan. 10, 2024

(65) Prior Publication Data
US 2024/0161544 A1  May 16, 2024

Related U.S. Application Data

(60) Continuation-in-part of application No. 18/183,932, filed on Mar. 14, 2023, now Pat. No. 11,877,831,
(Continued)

(51) Int. Cl.
*G06K 9/00* (2022.01)
*A61B 5/026* (2006.01)
(Continued)

(52) U.S. Cl.
CPC .......... *G06V 40/197* (2022.01); *A61B 5/0261* (2013.01); *A61B 5/1171* (2016.02);
(Continued)

(58) Field of Classification Search
CPC ........ G06V 40/40; G06V 40/45; G06V 40/10; G06V 40/00; G06V 40/14; G06V 40/16;
(Continued)

(56) References Cited

U.S. PATENT DOCUMENTS

D326,521 S    5/1992  Sawada
5,360,010 A   11/1994 Applegate
(Continued)

FOREIGN PATENT DOCUMENTS

CA    2827523 A1    8/2012
CA    3049901 A1    8/2012
(Continued)

OTHER PUBLICATIONS

Mayrovitz, Harvey N., Donald Larnard, and Gloria Duda. "Blood velocity measurement in human conjunctival vessels." Cardiovascular diseases 8.4 (1981): 509.
(Continued)

*Primary Examiner* — Atiba O Fitzpatrick
(74) *Attorney, Agent, or Firm* — Outlier Patent Attorneys, PLLC

(57) ABSTRACT

The present invention relates to biometric identification using a combination of static pattern characteristic unique to an individual and a measure of a dynamically changing blood flow characteristic for the individual. Images are acquired of the microvasculature of the outer eye (e.g. the sclera) which presents a unique pattern for each individual which can be determined using image processing and artificial intelligence (AI) techniques. A series of images are acquired of the microvasculature of the outer eye (e.g. the sclera) at a higher magnification thereby allowing for the determination of blood flow (e.g. velocity) characteristics using computer vision and AI techniques. The pattern and blood flow characteristics are used in combination to determine the identity of the individual.

15 Claims, 13 Drawing Sheets

Related U.S. Application Data which is a division of application No. 29/830,662, filed on Mar. 14, 2022.

(60) Provisional application No. 63/424,048, filed on Nov. 9, 2022, provisional application No. 63/319,738, filed on Mar. 14, 2022.

(51) Int. Cl.
- *A61B 5/1171* (2016.01)
- *G06Q 30/0251* (2023.01)
- *G06V 40/145* (2022.01)
- *G06V 40/18* (2022.01)
- *G06V 40/19* (2022.01)

(52) U.S. Cl.
CPC ....... *G06Q 30/0269* (2013.01); *G06V 40/145* (2022.01); *G06V 40/19* (2022.01)

(58) Field of Classification Search
CPC .... G06V 40/18; G06V 40/193; G06V 40/197; G06V 10/80; G06V 10/806; G06V 10/803; G06V 10/809; G06V 10/811; G06V 10/70; G06V 10/82; G06V 10/774–7796; G06V 10/454; G06T 2207/30041; G06T 2207/30101; G06T 2207/30104; G06T 2207/20081; G06T 2207/20084; G06T 9/002; G06T 5/60; A61B 3/14; A61B 3/145; A61B 3/00; G01N 2800/16; G01N 2800/162; G01N 2800/166; G01N 2800/168; G01N 29/4481; G06F 18/214–2155; G06F 7/023; G06F 40/16; G06N 3/08–0985; G06N 3/02–126; G06N 20/00–20; G06K 9/6256; G06K 9/6257; G06K 9/6259

See application file for complete search history.

(56) References Cited

U.S. PATENT DOCUMENTS

| | | | |
|---|---|---|---|
| 5,724,348 A | 3/1998 | Basso et al. | |
| D430,812 S | 9/2000 | Levin et al. | |
| 6,411,839 B1 | 6/2002 | Okinishi | |
| 7,327,860 B2 | 2/2008 | Derakhshani et al. | |
| D595,415 S | 6/2009 | Fukuzawa | |
| 8,279,042 B2 | 10/2012 | Beenau et al. | |
| 8,353,842 B2 | 1/2013 | Al-Ali et al. | |
| D682,718 S | 5/2013 | Azuma | |
| 8,733,933 B2 | 5/2014 | Hirose et al. | |
| 8,768,014 B2 | 7/2014 | Du et al. | |
| 8,953,837 B2 | 2/2015 | Gilad-Gilor | |
| 9,015,008 B2 | 4/2015 | Geva et al. | |
| 9,351,650 B2 | 5/2016 | Uji et al. | |
| 9,443,343 B2 | 9/2016 | Rhee et al. | |
| 9,575,723 B2 | 2/2017 | Sofia et al. | |
| 9,636,023 B2 | 5/2017 | Geesbreght et al. | |
| 10,039,445 B1* | 8/2018 | Torch | A61B 5/18 |
| 10,074,148 B2 | 9/2018 | Cashman et al. | |
| D833,624 S | 11/2018 | DeJong et al. | |
| 10,117,568 B2 | 11/2018 | Reisman et al. | |
| 10,143,373 B2 | 12/2018 | Gilad-Gilor | |
| 10,149,614 B2 | 12/2018 | Privitera et al. | |
| 10,226,217 B2 | 3/2019 | Dubin et al. | |
| 10,314,485 B2 | 6/2019 | Kiderman et al. | |
| 10,346,601 B2 | 7/2019 | Yun et al. | |
| D874,007 S | 1/2020 | Chang et al. | |
| D908,894 S | 1/2021 | Eslava et al. | |
| 11,013,455 B2 | 5/2021 | Teicher et al. | |
| 11,013,467 B2 | 5/2021 | Dubin et al. | |
| 11,020,015 B2 | 6/2021 | Rege et al. | |
| D930,163 S | 9/2021 | Turkieltaub et al. | |
| 11,363,952 B2 | 6/2022 | Venkatraman et al. | |
| 11,452,446 B2 | 9/2022 | Karargyris et al. | |
| 11,478,142 B2 | 10/2022 | Jackson et al. | |
| D982,759 S | 4/2023 | Qian et al. | |
| 2005/0033185 A1 | 2/2005 | Danen | |
| 2006/0253002 A1 | 11/2006 | Kolanko et al. | |
| 2010/0104168 A1 | 4/2010 | Dobbe | |
| 2012/0140170 A1 | 6/2012 | Hirose et al. | |
| 2012/0257164 A1 | 10/2012 | Zee et al. | |
| 2013/0023741 A1 | 1/2013 | Ayanruoh | |
| 2013/0070201 A1 | 3/2013 | Shahidi et al. | |
| 2013/0324810 A1 | 12/2013 | Gelland | |
| 2013/0331664 A1 | 12/2013 | Gilad-Gilor | |
| 2013/0338447 A1 | 12/2013 | Gilad-Gilor | |
| 2014/0018779 A1 | 1/2014 | Worrell et al. | |
| 2014/0044321 A1* | 2/2014 | Derakhshani | G06V 40/45 382/117 |
| 2014/0073880 A1 | 3/2014 | Boucher et al. | |
| 2014/0358011 A1 | 12/2014 | Jiang et al. | |
| 2015/0199783 A1 | 7/2015 | Cashman et al. | |
| 2015/0324568 A1* | 11/2015 | Publicover | H04N 23/80 726/19 |
| 2016/0012292 A1* | 1/2016 | Perna | G06V 40/193 382/117 |
| 2016/0117544 A1* | 4/2016 | Hoyos | G01B 11/22 348/78 |
| 2016/0220112 A1 | 8/2016 | Schmoll | |
| 2016/0335512 A1* | 11/2016 | Bradski | G06V 10/82 |
| 2017/0032092 A1 | 2/2017 | Mink et al. | |
| 2017/0112439 A1 | 4/2017 | Dubin et al. | |
| 2017/0235931 A1* | 8/2017 | Publicover | G06F 21/64 |
| 2017/0238798 A1 | 8/2017 | Isogai et al. | |
| 2017/0329916 A1 | 11/2017 | Bychkov et al. | |
| 2018/0000336 A1 | 1/2018 | Gilad-Gilor et al. | |
| 2018/0113988 A1 | 4/2018 | Desgranges et al. | |
| 2018/0140180 A1 | 5/2018 | Coleman | |
| 2018/0146911 A1 | 5/2018 | Teicher et al. | |
| 2018/0160887 A1 | 6/2018 | Hefez et al. | |
| 2018/0256087 A1 | 9/2018 | Al-Ali et al. | |
| 2018/0303343 A1 | 10/2018 | Dubin et al. | |
| 2018/0315193 A1 | 11/2018 | Paschalakis et al. | |
| 2019/0059728 A1 | 2/2019 | Gilad-Gilor | |
| 2019/0065722 A1* | 2/2019 | Kaehler | G06V 40/197 |
| 2019/0150762 A1 | 5/2019 | Chan et al. | |
| 2019/0279748 A1 | 9/2019 | Bychkov et al. | |
| 2019/0387983 A1 | 12/2019 | Script | |
| 2020/0029837 A1 | 1/2020 | Joudi | |
| 2020/0097080 A1* | 3/2020 | Kaehler | G06T 7/74 |
| 2020/0281534 A1 | 9/2020 | Geva et al. | |
| 2020/0305708 A1 | 10/2020 | Krueger | |
| 2020/0323427 A1 | 10/2020 | Gharib et al. | |
| 2020/0342245 A1* | 10/2020 | Lubin | G06V 40/70 |
| 2020/0359971 A1 | 11/2020 | Zhao et al. | |
| 2020/0405148 A1 | 12/2020 | Tran | |
| 2021/0030275 A1 | 2/2021 | Gilad-Gilor | |
| 2021/0073845 A1* | 3/2021 | Kaehler | G06V 10/95 |
| 2021/0161378 A1 | 6/2021 | Mowrey et al. | |
| 2021/0202094 A1 | 7/2021 | Bychkov et al. | |
| 2021/0236048 A1 | 8/2021 | Teicher et al. | |
| 2021/0236056 A1 | 8/2021 | Dubin et al. | |
| 2021/0393155 A1 | 12/2021 | Rogers et al. | |
| 2021/0393184 A1* | 12/2021 | Gallagher | G06F 3/165 |
| 2022/0005601 A1 | 1/2022 | Cox et al. | |
| 2022/0068154 A1* | 3/2022 | Breed | G06V 10/82 |
| 2022/0160309 A1 | 5/2022 | Poltorak | |
| 2022/0160991 A1 | 5/2022 | Craig et al. | |
| 2022/0165418 A1 | 5/2022 | Li et al. | |
| 2022/0175325 A1* | 6/2022 | Fukushima | A61B 5/7264 |
| 2022/0198831 A1 | 6/2022 | Coleman et al. | |
| 2022/0254500 A1 | 8/2022 | El-Baz et al. | |
| 2022/0351377 A1 | 11/2022 | Ehlers et al. | |
| 2022/0400989 A1 | 12/2022 | Myers | |
| 2023/0013271 A1 | 1/2023 | Siminou et al. | |
| 2023/0029585 A1* | 2/2023 | Chono | A61B 5/117 |
| 2023/0084637 A1* | 3/2023 | Matos | G06V 40/16 705/3 |
| 2023/0186686 A1* | 6/2023 | Hamid | G06V 40/171 382/115 |
| 2023/0187056 A1* | 6/2023 | Atkinson | G16H 50/20 351/246 |

(56) References Cited

U.S. PATENT DOCUMENTS

| | | | |
|---|---|---|---|
| 2023/0215532 A1 | 7/2023 | Fung | |
| 2023/0230232 A1 | 7/2023 | Liu et al. | |
| 2023/0350996 A1* | 11/2023 | O'Connor | G06V 40/172 |
| 2024/0037990 A1* | 2/2024 | Chono | G06V 40/197 |

FOREIGN PATENT DOCUMENTS

| | | | | |
|---|---|---|---|---|
| CA | 2986363 | A1 | 11/2016 | |
| CA | 2988683 | A1 | 12/2016 | |
| CA | 3041237 | A1 | 4/2017 | |
| CA | 3023829 | A1 | 11/2017 | |
| CN | 300699451 | A | 10/2007 | |
| CN | 101460097 | A * | 6/2009 | A61B 3/1233 |
| CN | 101411607 | B | 5/2010 | |
| CN | 109124686 | A | 1/2019 | |
| CN | 307246637 | A | 4/2022 | |
| EP | 2675345 | B1 | 3/2019 | |
| EP | 3297517 | B1 | 2/2021 | |
| EP | 3307142 | B1 | 3/2021 | |
| EP | 3813074 | A1 | 4/2021 | |
| EP | 2675351 | B1 | 6/2021 | |
| EP | 3834713 | A1 | 6/2021 | |
| EP | 3838111 | A1 | 6/2021 | |
| IN | 202111060104 | A | 12/2021 | |
| IN | 202141057189 | A | 2/2022 | |
| IN | 202241006220 | A | 11/2022 | |
| WO | 2010131550 | A1 | 11/2010 | |
| WO | 2011016029 | A3 | 2/2011 | |
| WO | 2011066546 | A1 | 6/2011 | |
| WO | 2012111012 | A1 | 8/2012 | |
| WO | 2012111013 | A1 | 8/2012 | |
| WO | 2013163443 | A2 | 10/2013 | |
| WO | 2016108229 | A1 | 7/2016 | |
| WO | 2016157173 | A1 | 10/2016 | |
| WO | 2016159523 | A1 | 10/2016 | |
| WO | 2016185463 | A1 | 11/2016 | |
| WO | 2016199134 | A1 | 12/2016 | |
| WO | 2017068573 | A1 | 4/2017 | |
| WO | 2017195203 | A2 | 11/2017 | |
| WO | 2017195203 | A3 | 11/2017 | |
| WO | 2019103912 | A2 | 5/2019 | |
| WO | 2020161709 | A1 | 8/2020 | |
| WO | 2020161710 | A1 | 8/2020 | |
| WO | 2020198154 | A1 | 10/2020 | |
| WO | 2021140503 | A1 | 7/2021 | |
| WO | 2021144790 | A1 | 7/2021 | |
| WO | 2022153320 | A1 | 7/2022 | |
| WO | 2023150229 | A1 | 8/2023 | |

OTHER PUBLICATIONS

Jo, Hang-Chan, et al. "Quantification of blood flow velocity in the human conjunctival microvessels using deep learning-based stabilization algorithm." Sensors 21.9 (2021): 3224.

Karanam, Veena C., et al. "Functional slit lamp biomicroscopy metrics correlate with cardiovascular risk." The ocular surface 17.1 (2019): 64-69.

Brennan, Paul F., et al. "Assessment of the conjunctival microcirculation for patients presenting with acute myocardial infarction compared to healthy controls." Scientific Reports 11.1 (2021): 7660.

Brennan, Paul F., et al. "Assessment of the conjunctival microcirculation in adult patients with cyanotic congenital heart disease compared to healthy controls." Microvascular Research 136 (2021): 104167.

Phelan, Ryan, "How the Courts treat Artificial Intelligence (AI) Patent Inventions: Through the Years since Alice," Mar. 12, 2021, Retrieved from the Internet: https://www.patentnext.com/2021/03/how-the-courts-treat-artificial-intelligence-ai-patent-inventions-through-the-years-since-alice/?utm_source=Mondaq&utm_medium=syndication&utm_campaign=LinkedIn-integration#, pp. 1-16.

Shieh-Newton, Terri, et al., "Patenting Considerations for Artificial Intelligence in Biotech and Synthetic Biology—Part 2: Key Issues in Patent Subject Matter Eligibility," Jan. 30, 2020, Retrieved from the Internet: https://www.mintz.com/insights-center/viewpoints/2231/2020-01-30-patenting-considerations-artificial-intelligence-biotech, pp. 1-5.

Landi, Heather, "AI startup that captures vital signs via phone cameras launches new corporate wellness solution," Jan. 11, 2021, Retrieved from the Internet: https://www.fiercehealthcare.com/tech/ai-health-startup-captures-vital-signs-via-phone-cameras-launches-new-corporate-wellness, pp. 1-2.

Ashrafuzzaman, Md, et al. "Heart attack detection using smart phone." International journal of technology enhancements and emerging engineering research 1.3 (2013): 23-27.

PCT International Search Report and Written Opinion dated Jun. 28, 2023, PCT International Application No. PCT/US23/64353, pp. 1-9.

Marcus C.B. Soori, Tricoder.Zero Linked in Post, Published on: Jul. 2023, LinkedIn.com, Retrieved from Internet: https ://www. li n ked in. com/posts/marcussoori_ tricorderzero-tricorder -health-activity-706357805437 517 4144-Ssi i?trk=public_profile_share_view (Year: 2023).

Nicole Sorkin, Tricorder.Zero Set to Revolutionize Telehealth & Telefitness, Published on: Mar. 25, 2023, Medium.com Retrieved from Internet: https://medium.com/@nicolesorkin/tricorder-zero-326a69a87f0 (Year: 2023).

* cited by examiner

SYSTEMS AND METHODS FOR BIOMETRIC IDENTIFICATION USING PATTERNS AND BLOOD FLOW CHARACTERISTICS OF THE OUTER EYE

CROSS-REFERENCE TO RELATED APPLICATIONS

This application is a continuation-in-part of U.S. patent application Ser. No. 18/183,932, filed Mar. 14, 2023, titled "SYSTEMS AND METHODS FOR ARTIFICIAL INTELLIGENCE BASED BLOOD PRESSURE COMPUTATION BASED ON IMAGES OF THE OUTER EYE", which claims the benefit of: U.S. Provisional Application 63/319,738, filed Mar. 14, 2022, titled "SYSTEMS AND METHODS FOR REMOTE AND AUTOMATED MEDICAL DIAGNOSIS," which is herein incorporated by reference in its entirety, U.S. Design application Ser. No. 29/830,662, filed Mar. 14, 2022, titled "CONSUMER ELECTRONICS DEVICE," which is herein incorporated by reference in its entirety, and U.S. Provisional Application 63/424,048, filed Nov. 9, 2022, titled "SYSTEMS AND METHODS FOR REMOTE AND AUTOMATED MEDICAL DIAGNOSIS," which is herein incorporated by reference in its entirety.

BACKGROUND

Field of Art

This disclosure relates generally to electronic medical devices and biometric authentication.

Discussion of the State of the Art

Biometric identification technologies generally rely on the principle that each individual has distinguishing characteristic(s) unique to that particular individual. In many cases this involves some sort of identifiable pattern (e.g. fingerprints, iris patterns, etc.) associated with a physical or biological characteristic of the individual. A problem with these patterns is that they can be artificially generated in order to fool biometric identification systems. For example, through advances in 3D printing technology, these patterns can be reproduced in 3D with the precision necessary to fool biometric scanners (e.g. via 3D models, contact lenses, etc.).

SUMMARY

The present invention relates, in part, to biometric identification using a combination of static biological or physiological characteristics and active or dynamic biological or physiological characteristics of an individual. In particular, an identity of an individual is determined using a combination of a pattern characteristic unique to an individual and a measure of a dynamically changing blood flow characteristic. For example, the microvasculature of the outer eye (e.g. in the scleral region) presents a unique pattern for each individual which can be detected as described herein and combined with blood velocity characteristics through at least a portion of the same microvasculature of the outer eye. This combination of measures allows for identification of an individual without being able to be faked by current technology. That is, while patterns alone are becoming increasingly reproducible by artificial means, the actual blood flow characteristics of a living individual cannot be faked.

One novel approach to biometric identification described herein includes obtaining a first image, from a first camera, of the vasculature of the outer eye of an individual, obtaining a series of second images at a higher magnification than the first image, from a second camera, of the vasculature of the outer eye of the individual, applying a first AI algorithm to analyze the images from the first camera to determine at least one pattern characteristic associated with the eye vasculature, applying a second AI algorithm to analyze the images from the second camera to determine at least one blood flow characteristic (e.g. velocity) within the eye vasculature, and applying a third AI algorithm to determine an identity of the individual based on the combination of the analysis of the at least one pattern characteristic and the at least one blood flow characteristic. In one aspect, the third AI algorithm is operable to compare the at least one pattern characteristic and the at least one blood flow characteristic with a database of previously established pattern characteristics and blood flow characteristics for a plurality of individuals in order to determine identity.

Currently, there are no known conventional approaches to biometric identification techniques or systems which rely on the combination of eye vasculature patterns and dynamic blood flow characteristics. The present approaches allow for contactless, real-time biometric identification from computer vision and AI processing of images of the outer eye which is not known to exist in the prior art.

BRIEF DESCRIPTION OF THE DRAWING FIGURES

The accompanying drawings illustrate several embodiments and, together with the description, serve to explain the principles of the invention according to the embodiments. It will be appreciated by one skilled in the art that the particular arrangements illustrated in the drawings are merely exemplary and are not to be considered as limiting of the scope of the invention or the claims herein in any way.

Figure 10:
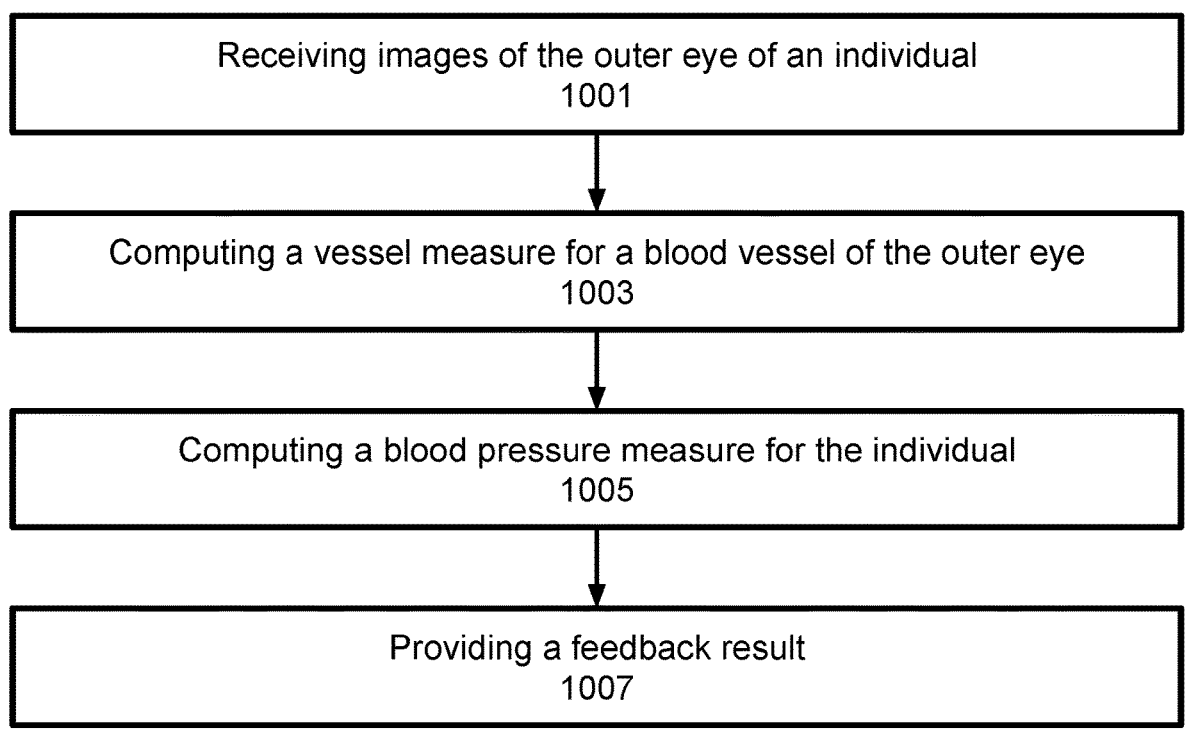
Figure 11A:
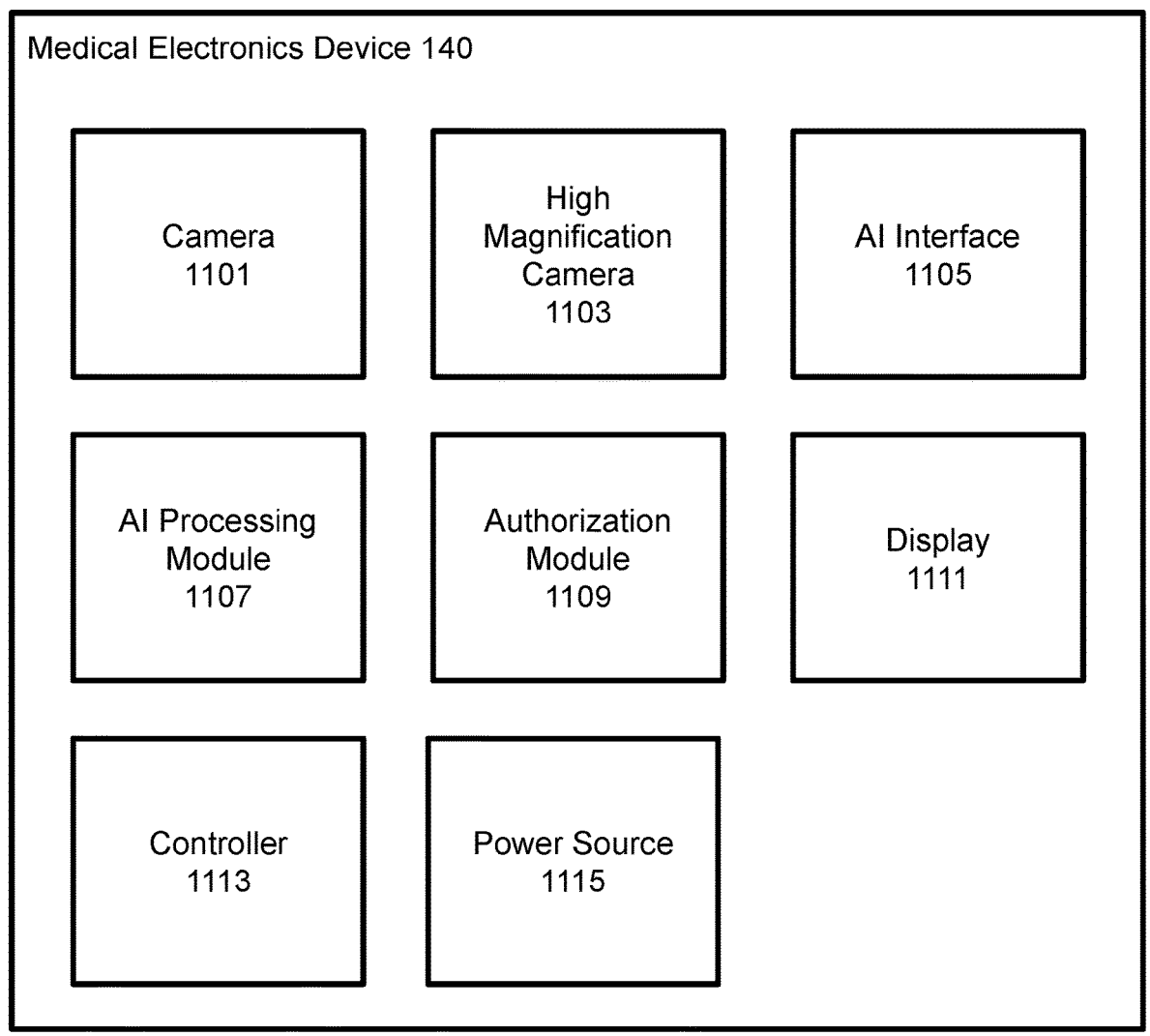
Figure 11B:
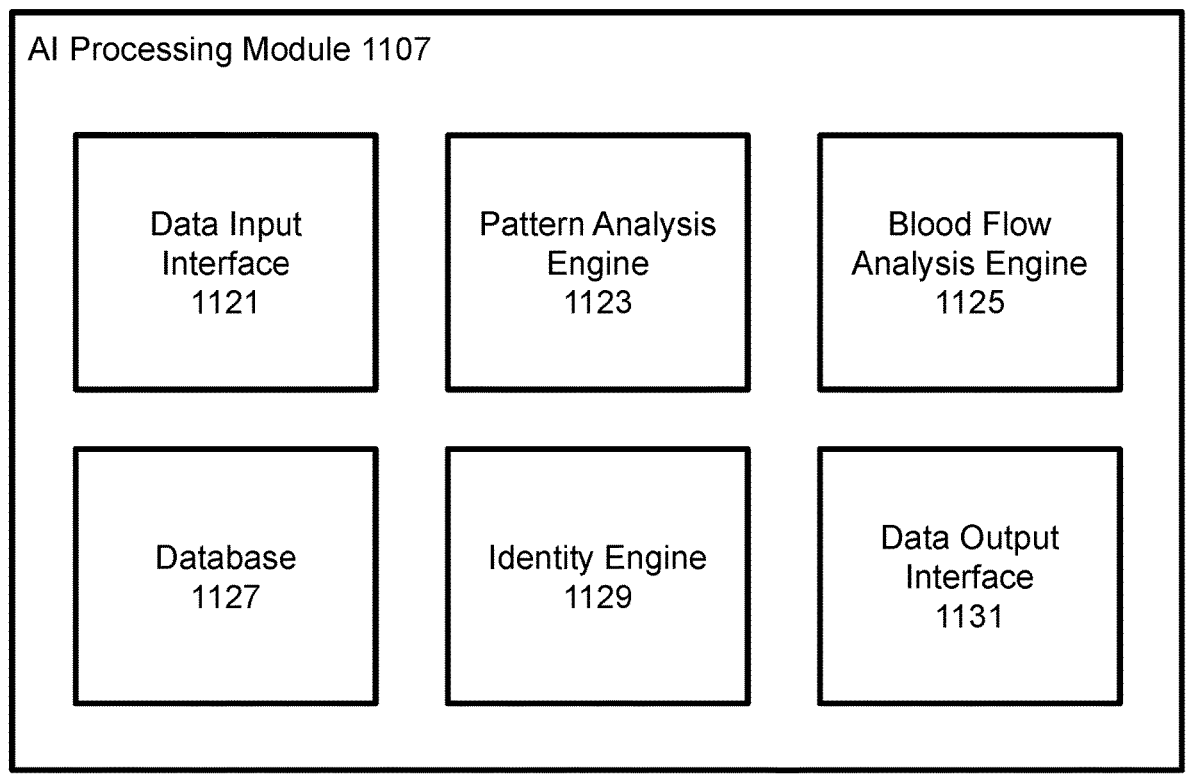
Figure 12:
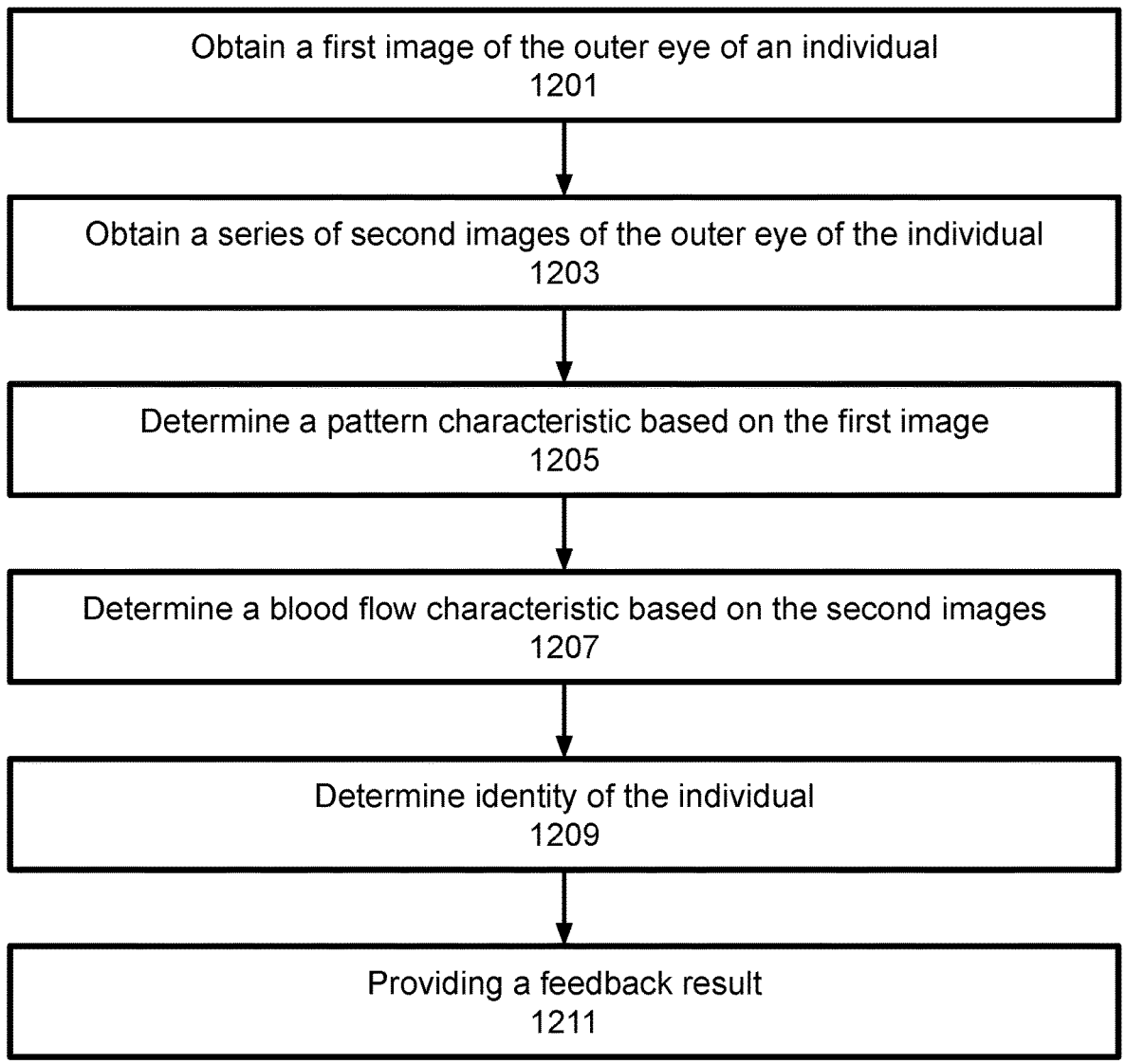

FIG. 10 illustrates an exemplary overview of a process for computing blood pressure based on images of the eye according to one exemplary embodiment of the inventive disclosure. FIG. 11A illustrates an exemplary medical electronics device in accordance with an exemplary embodiment of the invention. FIG. 11B illustrates an exemplary AI processing module in accordance with an exemplary embodiment of the invention. FIG. 12 illustrates a method of gathering and analyzing biometric information in accordance with an exemplary embodiment of the invention.

DETAILED DESCRIPTION OF EMBODIMENTS

The inventive systems and methods (hereinafter sometimes referred to more simply as "system" or "method") described herein facilitate remote and/or automated medical diagnosis. Specifically, a medical/consumer electronics device, comprising a plurality of sensors, may receive information from at least two sensors. The medical/consumer electronics device may transmit the information received from the at least two sensors over a network to a user device, which may further transmit the data to a remote server hosting a remote analysis platform. The remote server may use artificial intelligence (AI) and the information received from the at least two sensors to determine a diagnosis, an urgency level, and/or a recommendation and transmit a signal indicative of the determined diagnosis, urgency level, and/or recommendation over the network to the medical/consumer electronics device. The medical/consumer electronics device may display the determined diagnosis, urgency level, and/or recommendation. The present invention reduces time and expense associated with getting a medical diagnosis. The present invention facilitates medical diagnosis without exposing medical personnel to possibly contagious patients, and without users of the invention being exposed to possibly contagious patients or environments in public healthcare settings.

One or more different embodiments may be described in the present application. Further, for one or more of the embodiments described herein, numerous alternative arrangements may be described; it should be appreciated that these are presented for illustrative purposes only and are not limiting of the embodiments contained herein or the claims presented herein in any way. One or more of the arrangements may be widely applicable to numerous embodiments, as may be readily apparent from the disclosure. In general, arrangements are described in sufficient detail to enable those skilled in the art to practice one or more of the embodiments, and it should be appreciated that other arrangements may be utilized and that structural, logical, software, electrical and other changes may be made without departing from the scope of the embodiments. Particular features of one or more of the embodiments described herein may be described with reference to one or more particular embodiments or figures that form a part of the present disclosure, and in which are shown, by way of illustration, specific arrangements of one or more of the aspects. It should be appreciated, however, that such features are not limited to usage in the one or more particular embodiments or figures with reference to which they are described. The present disclosure is neither a literal description of all arrangements of one or more of the embodiments nor a listing of features of one or more of the embodiments that must be present in all arrangements.

Headings of sections provided in this patent application and the title of this patent application are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible embodiments and in order to more fully illustrate one or more embodiments. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the embodiments, and does not imply that the illustrated process is preferred. Also, steps are generally described once per aspect, but this does not mean they must occur once, or that they may only occur once each time a process, method, or algorithm is carried out or executed. Some steps may be omitted in some embodiments or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various embodiments in which, for example, functions may be executed out of order from that shown or discussed, including substantially concurrently or in reverse order, depending on the functionality involved, as would be understood by those having ordinary skill in the art.

Conceptual Architecture

Figure 1:
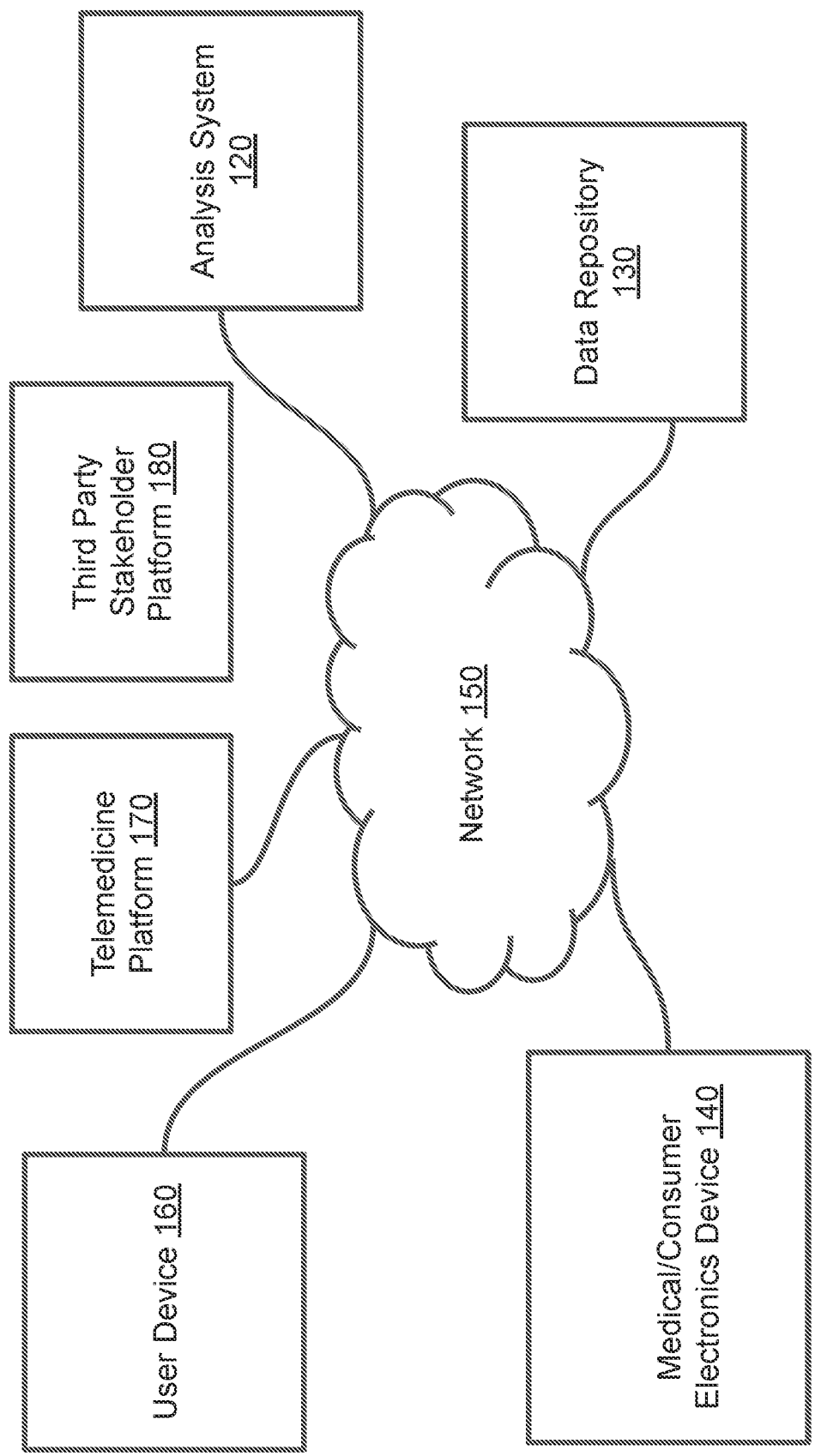
FIG. 1 illustrates an environment for remote and/or automated medical diagnosis in accordance with an exemplary embodiment of the invention.

FIG. 1 illustrates an environment for remote and/or automated medical diagnosis in accordance with an exemplary embodiment of the invention. The environment comprises a medical/consumer electronics device 140, an analysis system 120, a data repository 130, a network 150, a user device 160, a telemedicine platform 170, and a third party stakeholder platform 180. The various computing devices described herein are exemplary and for illustration purposes only. The system may be reorganized or consolidated, as understood by a person of ordinary skill in the art, to perform the same tasks on one or more other servers or computing devices without departing from the scope of the invention.

The medical/consumer electronics device 140 may comprise a plurality of sensors. The medical/consumer electronics device 140 may comprise a browser for accessing a web application hosted on the analysis system 120. The medical/consumer electronics device 140 may comprise an application for interacting with a web application hosted on the analysis system 120. The medical/consumer electronics device 140 may comprise an application obtained from the analysis system 120. The medical/consumer electronics device 140 may transmit data collected from the plurality of sensors to the analysis system 120 via the network 150. The medical/consumer electronics device 140 may receive a diagnosis, an urgency level, and/or a recommendation from the analysis system 120 via the network 150. The medical/consumer electronics device 140 may comprise a device a consumer uses at home. The medical/consumer electronics device 140 may comprise sensors as attachments to a user device, such as a laptop or smartphone. The medical/consumer electronics device 140 may comprise a device used at a medical office. For example, the medical/consumer electronics device 140 may suggest to a doctor drugs to prescribe to a patient, specialists to refer a patient to, imaging or other diagnosis procedures to suggest for a patient, admittance of a patient to a hospital or emergency room, etc. The medical/consumer electronics device 140 may comprise a device for collecting biometrics to determine if access to an area should be given to an individual. The medical/consumer electronics device 140 may transfer data to a remote security server (not shown) for biometric matching. The medical/consumer electronics device 140 may retrieve data from the remote security server for biometric matching. The medical/consumer electronics device 140 may be used in advertising to determine that a user is positioned in front of a digital billboard (not shown). The medical/consumer electronics device 140 may identify the user and/or characteristics of the user and facilitate targeted ads to the user based on the identified user and/or identified characteristics. The medical/consumer electronics device 140 may transfer data to a remote ad server (not shown) for targeted advertising. The medical/consumer electronics device 140 may retrieve data from the remote ad server for targeted advertising. The medical/consumer electronics device 140 may cause the digital billboard to display a targeted advertisement for the user. The medical/consumer electronics device 140 will be described in greater detail in reference to FIG. 2. The medical device/consumer electronics 140 device may comprise sensors as wired or wireless attachments to a user device, such as a laptop, tablet, or smartphone. The medical/consumer electronics/advertising/security device may comprise a device for collecting biometrics to determine if access to an area should be given to an individual. The medical/consumer electronics/advertising/security device may be used in advertising to determine that a user is positioned in front of a digital billboard.

The analysis system 120 may comprise a remote server. The analysis system 120 may comprise one or more computing devices. The analysis system 120 may comprise a cloud computing environment. The analysis system 120 may host a website. The analysis system 120 may host a web application. The analysis system 120 may provide applications, such as mobile applications, for download by the medical/consumer electronics device 140 via the network 150. The analysis system 120 may receive information from sensors from the medical/consumer electronics device 140 via the network 150. The analysis system 120 may determine a diagnosis, an urgency level, and/or a recommendation based on the received information from sensors. The analysis system 120 may transmit the determined diagnosis, urgency level, and/or recommendation to the medical/consumer electronics device 140 via the network 150. The analysis system 120 may data, such as artificial intelligence (AI) training data, from the data repository 130 via the network 150. The analysis system 120 may store data, such as data received from a particular medical/consumer electronics device and associated determined diagnoses, urgency levels, and/or recommendations, in the data repository 130 via the network 150. The analysis system 120 will be described in greater detail in reference to FIG. 3. The analysis system may send or receive data, such as artificial intelligence training or analyzed data or results (for example and without limitation, diagnosis, urgency level, and/or recommendation), to or from the data repository via the network. The analysis system may transmit the determined diagnosis, urgency level, and/or recommendation to the medical device or a device connected to it (wired or wirelessly) via the network.

The data repository 130 may comprise data storage. The data repository 130 may comprise AI training data. The data repository 130 may comprise data sets. The data sets may associate information received from particular medical/consumer electronics devices 140, such as information from sensors. The data sets may comprise a diagnosis, urgency level, and/or recommendation associated with information received from a particular medical/consumer electronics device 140. The data repository 130 may comprise biometric data. The data repository 130 may comprise information for targeting advertising. The data repository may comprise one or more AI engines and/or algorithms.

The network 150 may facilitate communication between the medical/consumer electronics device 140, the analysis system 120, the data repository 130, the user device 160, the telemedicine platform 170, and the third party stakeholder platform 180, as well as other devices, as would be understood by a person of ordinary skill in the art.

The network 150 generally represents a network or collection of networks (such as the Internet or a corporate intranet, or a combination of both) over which the various components illustrated in FIG. 1 (including other components that may be necessary to execute the system described herein, as would be readily understood to a person of ordinary skill in the art). In particular embodiments, network 150 is an intranet, an extranet, a virtual private network (VPN), a local area network (LAN), a wireless LAN (WLAN), a wide area network (WAN), a metropolitan area network (MAN), a portion of the Internet, or another network 150 or a combination of two or more such networks 150. One or more links connect the systems and databases described herein to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable network 150, and any suitable link for connecting the various systems and databases described herein.

The network 150 connects the various systems and computing devices described or referenced herein. In particular embodiments, network 150 is an intranet, an extranet, a virtual private network (VPN), a local area network (LAN), a wireless LAN (WLAN), a wide area network (WAN), a metropolitan area network (MAN), a portion of the Internet, or another network or a combination of two or more such networks 150. The present disclosure contemplates any suitable network 150.

One or more links couple one or more systems, engines or devices to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable links coupling one or more systems, engines or devices to the network 150.

In particular embodiments, each system or engine may be a unitary server or may be a distributed server spanning multiple computers or multiple datacenters. Systems, engines, or modules may be of various types, such as, for example and without limitation, web server, news server, mail server, message server, advertising server, file server, application server, exchange server, database server, or proxy server. In particular embodiments, each system, engine or module may include hardware, software, or embedded logic components or a combination of two or more such components for carrying out the appropriate functionalities implemented or supported by their respective servers. For example, a web server is generally capable of hosting websites containing web pages or particular elements of web pages. More specifically, a web server may host HTML files or other file types, or may dynamically create or constitute files upon a request, and communicate them to one or more computing device(s) or other devices in response to HTTP or other requests from one or more computing device(s) or other devices. A mail server is generally capable of providing electronic mail services to various one or more computing device(s) or other devices. A database server is generally capable of providing an interface for managing data stored in one or more data stores.

In particular embodiments, one or more data storages may be communicatively linked to one or more servers via one or more links. In particular embodiments, data storages may be used to store various types of information. In particular embodiments, the information stored in data storages may be organized according to specific data structures. In particular embodiments, each data storage may be a relational database. Particular embodiments may provide interfaces that enable servers or clients to manage, e.g., retrieve, modify, add, or delete, the information stored in data storage.

The system may also contain other subsystems and databases, which are not illustrated in FIG. 1, but would be readily apparent to a person of ordinary skill in the art. For example, the system may include databases for storing data, storing features, storing outcomes (training sets), and storing models. Other databases and systems may be added or subtracted, as would be readily understood by a person of ordinary skill in the art, without departing from the scope of the invention.

A first user may feel warm, have shortness of breath, a cough, and chest pains. The first user may use a thermometer of a first medical/consumer electronics device to take a body temperature. The first user may use a pulse oximeter of the first medical/consumer electronics device to take a heart rate and an oxygen saturation level. The first user may use a stethoscope of the first medical/consumer electronics device to listen to chest sounds. The body temperature may be 102 degrees Fahrenheit. The heart rate may be 92 beats per minute. The oxygen saturation level may be 89%. The chest sounds may comprise congested sounds. The first medical/consumer electronics device may transmit the body temperature, heart rate, oxygen saturation level, and chest sounds over a network to a telemedicine platform. The telemedicine platform may use artificial intelligence (AI) to determine a possible infection, likely related to a respiratory system. The telemedicine platform may determine that the possible causes comprise bacterial pneumonia, viral pneumonia, COVID-19, exacerbation of COPD, etc. The telemedicine platform may assign an urgency level of 4, on a scale of 1-5, 5 being the most urgent. The telemedicine platform may recommend contacting physician urgently and if unable to do so, proceed to urgent medical care facility. In one embodiment, the data repository may comprise an AI server/system/platform that analyzes the data and sends the results to the telemedicine platform and/or the medical/consumer electronics/security/advertising device and/or any device connected to it (wired or wireless).

A second user may develop pains over the chest with numbness in the left arm, be sweating, feel very weak and have shortness of breath. The second user may use a thermometer of a second medical/consumer electronics device to take a body temperature. The second user may use a pulse oximeter of the second medical/consumer electronics device to take a pulse and an oxygen saturation level. The second user may use a high-magnification camera of the second medical/consumer electronics device to determine a blood pressure. The second user may use an electrocardiogram (EKG) to take heart measurements. The body temperature may be 80 degrees Fahrenheit. The pulse may be 106 beats per minute. The oxygen saturation level may be 90%. The blood pressure may be 90/60. The EKG heart measurements may reveal a heart rate of 92 beats per minute, an irregular heart beat, and an abnormal EKG pattern. The second medical/consumer electronics device may transmit the body temperature, pulse, oxygen saturation level, blood pressure, and EKG heart measurements over a network to a telemedicine platform. The telemedicine platform may use artificial intelligence (AI) to determine possible conditions comprise a heart attack, blood clots in lungs, pericarditis, etc. The telemedicine platform may assign an urgency level of 5, on a scale of 1-5, 5 being the most urgent. The telemedicine platform may recommend contacting a doctor urgently, proceeding to an urgent care facility promptly, or calling 911. In one embodiment, the data repository may comprise an AI server/system/platform that analyzes the data and sends the results to the telemedicine platform and/or the medical/consumer electronics/security/advertising device and/or any device connected to it (wired or wireless).

A third user may feel nausea and have vomiting, pains in the abdomen, very dark urine, and yellow skin. The third user may use a thermometer of a third medical/consumer electronics device to take a body temperature. The third user may use a pulse oximeter of the third medical/consumer electronics device to take a pulse and an oxygen saturation level. The third user may use a high-magnification camera of the third medical/consumer electronics device to take one or more eye images. The body temperature may be 99 degrees Fahrenheit. The pulse may be 92 beats per minute. The oxygen saturation level may be 96%. The blood pressure may be 90/60. The one or more eye images may reveal yellow sclera. The telemedicine platform may use artificial intelligence (AI) to determine possible conditions comprise gallbladder inflammation, gallstones, pancreatic tumor causing bile blockage, etc. The telemedicine platform may assign an urgency level of 3, on a scale of 1-5, 5 being the most urgent. The telemedicine platform may recommend contacting a telemedicine physician. The telemedicine platform may initiate a call with a telemedicine physician. In one embodiment, the data repository may comprise an AI server/system/platform that analyzes the data and sends the results to the telemedicine platform and/or the medical/consumer electronics/security/advertising device and/or any device connected to it (wired or wireless).

A fourth user may work in a secure area of an office building or seek access to a virtual secure area. In order to access the secure area, a fourth medical/consumer electronics device may be on an adjustable stand, such that a height of a high-magnification camera of the fourth medical/consumer electronics device may be adjusted to an eye level of the fourth user, or may be part of a network-connected wearable headset. The high-magnification camera may take a picture or video of the unique, individualized pattern of conjunctival vessels, and/or white space between conjunctival vessels, within a predefined area of at least 0.25 millimeter squared and maximum 4 inches squared, of the fourth user to identify the fourth user as a user with access credentials to the physical or virtual secure area and allow the fourth user to have access to the secure area.

A fifth user may stand in front of a digital billboard. A fifth medical/consumer electronics device associated with the digital billboard may comprise a variety of sensors for a user, including one or more microphones for detecting noise a user makes, a thermometer to detect a user's body temperature, a barometer to detect a change in atmospheric pressure due to the presence of a user, a bluetooth receiver for detecting and/or identifying a user device a user may carry, and/or multiple cameras for identifying users and/or user features and/or user object features, such as a vehicle license plate, if the user is driving towards of a digital billboard. In one embodiment, conjunctival vasculature and/or white space between conjunctival vasculature may be measured. Additionally, data from digital billboard sensors may be combined from data on in-house and/or affiliated and/or non-affiliated servers from the applicant and/or other providers related to the user (with whom the user has previously shared data), which the user has previously provided permission for 3rd parties to access for the purpose of targeted advertising. The variety of sensors may be used to identify the fifth user and/or characteristics of the fifth user. Based on the identity of the fifth user and/or identified characteristics of the fifth user, a targeted advertisement for the fifth user may be selected and displayed on the digital billboard. Speakers associated with the digital billboard may call out to the fifth user by name to get the attention of the fifth user.

user devices 160 refers to computing devices that may be used to display user interface elements associated that may be generated by the relational database engine 102. The user device 160 (herein referred to as user input device, user device, or client device) may include, generally, a computer or computing device including functionality for communicating (e.g., remotely) over the network 150. user devices 160 may be a server, a desktop computer, a laptop computer, personal digital assistant (PDA), an in- or out-of-car navigation system, a smart phone or other cellular or mobile phone, or mobile gaming device, among other suitable computing devices. user devices 160 may execute one or more client applications, such as a web browser (e.g., Microsoft Windows Internet Explorer, Mozilla Firefox, Apple Safari, Google Chrome, and Opera, etc.), or a dedicated application to submit user data, or to make prediction queries over the network 150.

In particular embodiments, each user device 160 may be an electronic device including hardware, software, or embedded logic components or a combination of two or more such components and capable of carrying out the appropriate functions implemented or supported by the user device 160. For example and without limitation, user device 160 may be a desktop computer system, a notebook computer system, a netbook computer system, a handheld electronic device, or a mobile telephone. The present disclosure contemplates any user device as the user device 160. The user device 160 may enable a network user at the user device 160 to access network 150. The user device 160 may enable its user to communicate with other users at other client devices.

The user device 160 may have a web browser, such as MICROSOFT INTERNET EXPLORER, GOOGLE CHROME or MOZILLA FIREFOX, and may have one or more add-ons, plug-ins, or other extensions, such as TOOLBAR or YAHOO TOOLBAR. The user device 160 may enable a user to enter a Uniform Resource Locator (URL) or other address directing the web browser to a server, and the web browser may generate a Hyper Text Transfer Protocol (HTTP) request and communicate the HTTP request to server. The server may accept the HTTP request and communicate to the user device 160 one or more Hyper Text Markup Language (HTML) files responsive to the HTTP request. The user device 160 may render a web page based on the HTML files from server for presentation to the user. The present disclosure contemplates any suitable web page files. As an example and not by way of limitation, web pages may render from HTML files, Extensible Hyper Text Markup Language (XHTML) files, or Extensible Markup Language (XML) files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a web page encompasses one or more corresponding web page files (which a browser may use to render the web page) and vice versa, where appropriate.

The user device 160 may also include an application that is loaded onto the user device 160. The application obtains data from the network 150 and displays it to the user within the application interface.

This disclosure contemplates any suitable number of user devices 160, including computing systems taking any suitable physical form. As example and not by way of limitation, computing systems may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, or a combination of two or more of these. Where appropriate, the computing system may include one or more computer systems; be unitary or distributed; span multiple locations; span multiple machines; or reside in a cloud, which may include one or more cloud components in one or more networks. Where appropriate, one or more computing systems may perform without substantial spatial or temporal limitation one or more steps of one or more methods described or illustrated herein. As an example, and not by way of limitation, one or more computing systems may perform in real time or in batch mode one or more steps of one or more methods described or illustrated herein. One or more computing systems may perform at different times or at different locations one or more steps of one or more methods described or illustrated herein, where appropriate. In one embodiment, the user device 150 communicates and/or interfaces with the medical/consumer electronics device to obtain data from the device via a communication channel disclosed herein, and may transmit that data to the analysis system 120 via a communication channel disclosed herein.

The telemedicine platform 160 enables communication between a patient and a provider such as a physician, nurse practitioner, etc. The telemedicine platform 160 may enable communication amongst any user associated with any of the devices described herein.

All of the devices described herein may include a communication module for communicating with other devices described herein as well as devices that are not disclosed herein. The communication module may communicate via a wired connection (e.g., including a physical connection such as a cable with a suitable connection interface such as USB, mini-USB, etc.) and/or a wireless network (e.g., through NFC, Bluetooth, WiFi, RFID, or any type of digital network that is not connected by cables). For example, devices may directly communicate with each other in pairwise connection (1:1 relationship), or in a hub-spoke or broadcasting connection ("one to many" or 1:m relationship). As another example, the devices may communicate with each other through mesh networking connections (e.g., "many to many", or m:m relationships), such as through Bluetooth mesh networking. Wireless communication may use any of a plurality of communication standards, protocols, and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), or any other suitable communication protocol. Some wireless network deployments may combine networks from multiple cellular networks (e.g., 3G, 4G, 5G) and/or use a mix of cellular, WiFi, and satellite communication.

The third party stakeholder platform 180 may comprise third parties such as, but not limited to, insurance companies, hospitals, pharmacies, etc. In one embodiment, the third party stakeholder platform 180 may receive information from the medical/consumer electronics device 140, telemedicine platform 170, analysis system 120, and/or data repository 130 for preventive health purposes, overall healthcare cost savings, and reduced deductibles/premiums, etc.

Medical/Consumer Electronics Device

Figure 2:
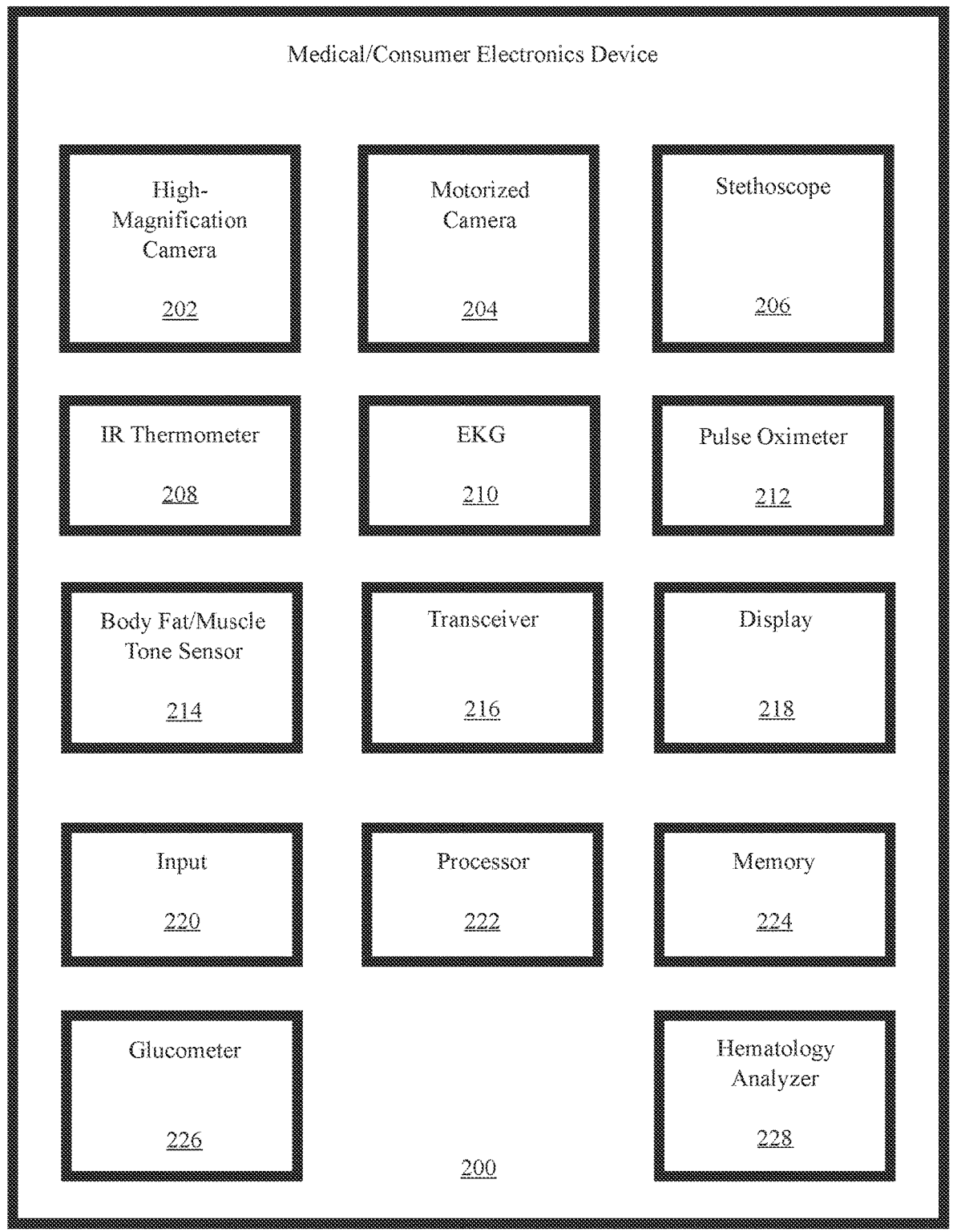
FIG. 2 illustrates an example medical/consumer electronics device in accordance with an exemplary embodiment of the invention.

FIG. 2 illustrates an example medical/consumer electronics device 200 in accordance with an exemplary embodiment of the invention. The example medical/consumer electronics device 200 may receive information about a user from sensors. The example medical/consumer electronics device 200 may receive information about a user from the sensors for medical diagnosis purposes. The example medical/consumer electronics device 200 may receive information about a user from the sensors for identification purposes. The example medical/consumer electronics device 200 may receive information about a user from the sensors for targeted advertisement purposes. The example medical/consumer electronics device 200 may be the same or similar to the medical/consumer electronics device 140 in FIG. 1. The example medical/consumer electronics device 200 comprises a high-magnification camera 202, a motorized camera 204, a stethoscope 206, an infrared (IR) thermometer 208, an electrocardiogram (EKG) 210, a pulse oximeter 212, a body fat and/or muscle tone sensor 214, a transceiver 216, a display 218, an input device 220, a processor 222, memory 224, a glucometer 226, and a hematology analyzer 228. Although not shown, an exemplary medical/consumer electronics device may also comprise one or more microphones for detecting noise a user makes, one or more speakers for providing audio to a user, a barometer to detect a change in atmospheric pressure due to the presence of a user, a tongue depressor to clear a user's mouth for throat images and/or video, a urine analyzer to detect and/or quantify a number of analytes including bilirubin, protein, glucose and red blood cells in a user's urine, and/or a bluetooth receiver for detecting and/or identifying a user device a user may carry. Although only one of each sensor is shown in the example medical/consumer electronics device 200, an exemplary medical/consumer electronics device may comprise multiple types of a particular sensor. For example, an exemplary medical/consumer electronics device may comprise multiple high-magnification cameras. Other systems and databases may be used, as would be readily understood by a person of ordinary skill in the art, without departing from the scope of the invention. The example medical device may receive information about a user from the sensors for informational and/or entertainment purposes. In one embodiment, the sensors may include one or more speakers and/or one or more microphones, in addition to the ones described herein.

The high-magnification camera 202 may comprise one or more light-emitting diodes (LEDs). The high-magnification camera 202 may capture high quality images and/or video of a patient's eye and/or skin. The high-magnification camera 202 may zoom in on vessels (veins/venules and/or arteries/arterioles) and/or the space in between such vessels in a patient's eye and capture video of blood flowing through eye vessels (veins/venules and/or arteries/arterioles) and/or the space in between such vessels to be used to calculate a blood pressure for the user. The high-magnification camera 202 may capture a user's conjunctival vasculature to be used for identification of the user and/or advertising. The high-magnification camera 202 may capture an object associated with a user, such as a vehicle license plate, to be used for identification of the user.

The motorized camera 204 may comprise one or more LEDs. The motorized camera 204 may extend or retract as needed to get a clear position for image and/or video capturing. The motorized camera 204 may capture high quality images and/or video of a patient's ear, nose, and/or throat. The motorized camera may also be used as a tongue depressor.

The stethoscope 206 may be used to capture audio from a patient's heart. The stethoscope 206 may be used to capture audio from a patient's lungs. The stethoscope 206 may be used to capture audio from a patient's arteries. The stethoscope 206 may be used to capture audio from a patient's vessels (veins/venules and/or arteries/arterioles) and/or the space in between such vessels. The IR temperature 208 may capture a user's body temperature. The EKG 210 may comprise diodes. The EKG 210 may capture electrical signals in a patient's heart. The pulse oximeter 212 may capture a patient's pulse. The pulse oximeter 212 may capture a patient's oxygen saturation level. The body fat and/or muscle tone sensor 214 may capture a patient's body fat. The body fat and/or muscle tone sensor 214 may capture a patient's muscle tone.

The transceiver 216 may send and receive data to a remote server over a network. For example, the transceiver 216 may send a signal indicative of information received from sensors of the medical/consumer electronics device 200 in FIG. 2 over the network 150 in FIG. 1 to the analysis system 120 in FIG. 1. For example, the transceiver 216 may receive a signal indicative of a diagnosis, an urgency level, and/or a recommendation from the analysis system 120 via the network 150. The transceiver 216 may prepare information received from sensors of the medical/consumer electronics device 200 into a format transmissible over a network, such as the network 150 and ultimately consumable by a remote server, such as the analysis system 120. The transceiver 216 may receive information from a network, such as the network 150, and prepare the information in a format consumable by the processor 222.

The display 218 may display information captured from sensors of the medical/consumer electronics device 200. The display 218 may display information input via the input 220 such as a patient's information (e.g., name, height, weight, etc.). The display 218 may display information received from a remote server, such as the analysis system 120 in FIG. 1. The input 220 may comprise keyboard (e.g., physical keyboard, virtual keyboard, projection keyboard, etc.), mouse, joystick, etc. The input 220 may be used to enter text, make selections, etc. The processor 222 may execute instructions stored in memory 224, such as an application to access the analysis system 120.

The glucometer 226 may receive strips containing a blood sample. The glucometer 226 may determine a concentration of glucose in a blood sample. The hematology analyzer 228 may receive a blood sample. The hematology analyzer 228 may analyze cells in a blood sample.

Analysis System

Figure 3:
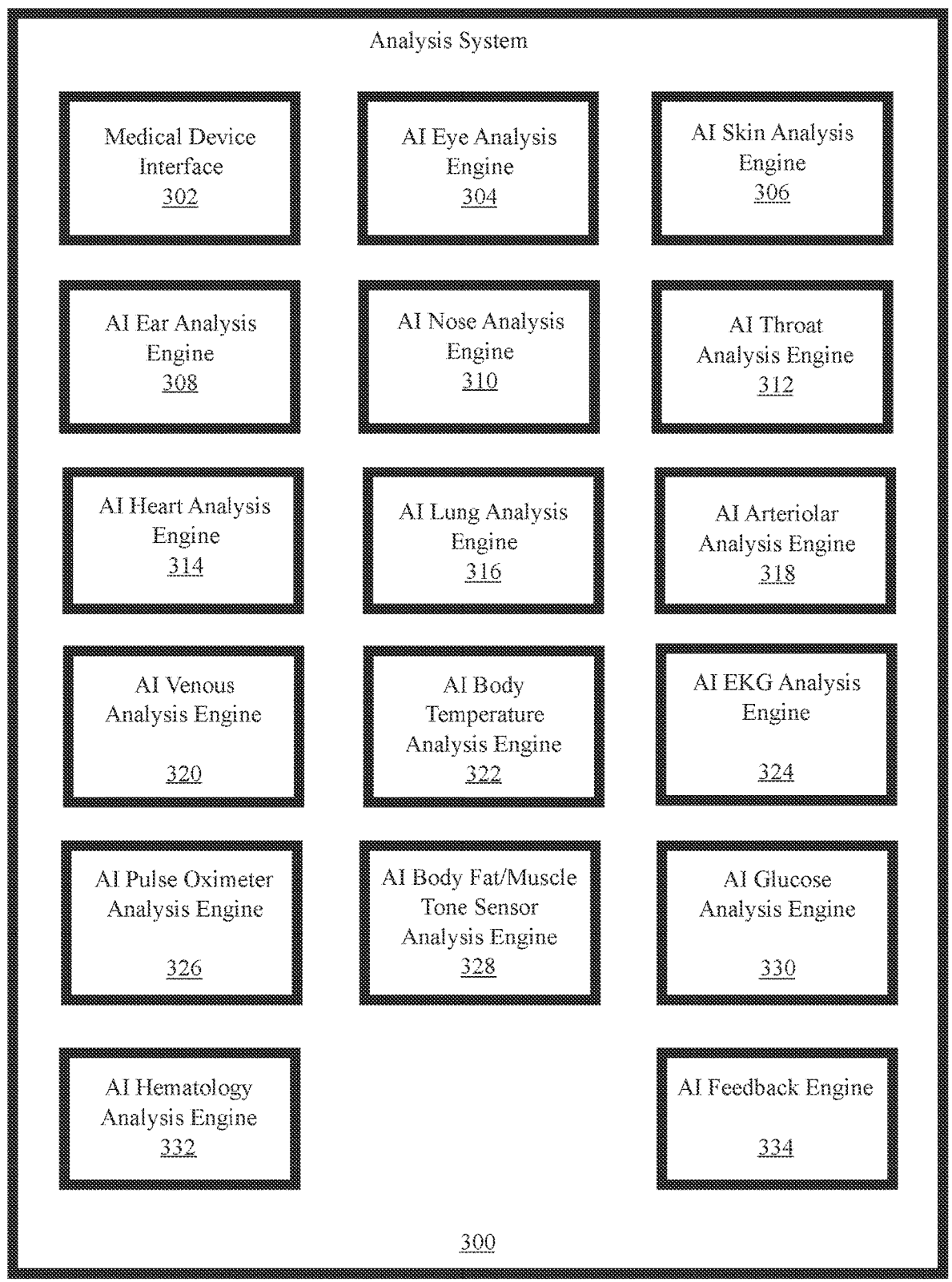
FIG. 3 illustrates an example telemedicine platform in accordance with an exemplary embodiment of the invention.

FIG. 3 illustrates an example analysis system 300 in accordance with an exemplary embodiment of the invention. The example analysis system 300 may receive a signal from a medical/consumer electronics device, such as the medical/consumer electronics device 140 in FIG. 1, via a network, such as the network 150 in FIG. 1, wherein the signal comprises information from sensors of the medical/consumer electronics device. The example analysis system 300 may use information from sensors of the medical/consumer electronics device to determine a diagnosis, an urgency level, and/or a recommendation. The example analysis system 300 may transmit a signal comprising the determined diagnosis, urgency level, and/or recommendation via the network, such as the network 150, to the medical/consumer electronics device, such as the medical/consumer electronics device 140. The example analysis system 300 may be the same or similar to the analysis system 120 in FIG. 1. The example analysis system 300 comprises one or more artificial intelligence (AI) modules. The AI modules may use training data to create a model for determining outputs (e.g., diagnoses, urgency levels, recommendations, etc.) for specific inputs. The AI modules may update models based on feedback from responses, creating a feedback loop that continually improves future results based on past results. The example analysis system 300 comprises a medical/consumer electronics device interface 302, an AI eye analysis engine 304, an AI skin analysis engine 306, an AI ear analysis engine 308, an AI nose analysis engine 310, an AI throat analysis engine 312, an AI heart analysis engine 314, an AI lung analysis engine 316, an AI arteriolar analysis engine 318, an AI venous analysis engine 320, an AI body temperature analysis engine 322, an AI electrocardiogram (EKG) analysis engine 324, an AI pulse oximeter analysis engine 326, an AI body fat and/or muscle tone sensor analysis engine 328, an AI glucose analysis engine 330, an AI hematology analysis engine 332, and an AI feedback engine 334. Other systems and databases may be used, as would be readily understood by a person of ordinary skill in the art, without departing from the scope of the invention.

The medical/consumer electronics device interface 302 may prepare information intended for a medical/consumer electronics device, such as the medical/consumer electronics device 140 in FIG. 1, into a format transmissible over a network, such as the network 150 in FIG. 1, and ultimately consumable by the medical/consumer electronics device. The medical/consumer electronics device interface 302 may receive information from a network, such as the network 150, and prepare the information in a format consumable by the example analysis system 300.

The AI eye analysis engine 304 may use computer vision to interpret images and/or video of an eye taken by a camera, such as the high-magnification camera 202 in FIG. 2. The AI eye analysis engine 304 may identify a possibility of one or more of conjunctivitis, iritis, subconjunctival hemorrhage, scleral lesions, jaundice (icterus), liver drainage problems, bile drainage problems, hepatitis, gallbladder attacks, bile blockage from gallstones, cancer of the pancreas, cancer of the bile ducts, stye (chalazion), allergies, etc. The AI eye analysis engine 304 may determine conjunctival vessel velocity by examining multiple time stamped eye images or eye video. The AI eye analysis engine 304 may determine a blood pressure based on the determined conjunctival vessel velocity. The AI eye analysis engine 304 may determine an identity by matching conjunctival vessel patterns (including, for example, Conjunctival vessel blood velocity), which could include the spaces in between conjunctival vessels. The AI eye analysis engine 304 may use AI to determine a state or condition. The AI eye analysis engine 304 may use AI to determine a range of possible states or conditions. The AI eye analysis engine 304 may associate a probability with each determined state or condition. Exemplary processing employed by the AI eye analysis engine 304 may be found below in association with FIG. 10 and the corresponding description.

The AI skin analysis engine 306 may use computer vision to interpret images and/or video of skin taken by a camera, such as the high-magnification camera 202 in FIG. 2. The AI skin analysis engine 306 may identify a possibility of one or more of rashes, hives, poison ivy, shingles, tumors, melanoma, bruises, petechiae, leg or other edema, ulcers, bed sores, etc. The AI skin analysis engine 306 may use AI to determine a state or condition. The AI skin analysis engine 306 may use AI to determine a range of possible states or conditions. The AI skin analysis engine 306 may associate a probability with each determined state or condition.

The AI ear analysis engine 308 may use computer vision to interpret images and/or video of an ear taken by a camera, such as the motorized camera 204 in FIG. 2. The AI ear analysis engine 308 may identify a possibility of one or more of neoplasia, perforation, tympanosclerosis, middle ear effusion, retracted eardrum, haemotympanum, etc. The AI ear analysis engine 308 may use AI to determine a state or condition. The AI ear analysis engine 308 may use AI to determine a range of possible states or conditions. The AI ear analysis engine 308 may associate a probability with each determined state or condition.

The AI nose analysis engine 310 may use computer vision to interpret images and/or video of a nose taken by a camera, such as the motorized camera 204 in FIG. 2. The AI nose analysis engine 310 may identify a possibility of one or more of obstruction, sinusitis, rhinitis, polyps, adenoids, cancer, etc. The AI nose analysis engine 310 may use AI to determine a state or condition. The AI nose analysis engine 310 may use AI to determine a range of possible states or conditions. The AI nose analysis engine 310 may associate a probability with each determined state or condition.

The AI throat analysis engine 312 may use computer vision to interpret images and/or video of a throat taken by a camera, such as the motorized camera 204 in FIG. 2. The AI throat analysis engine 312 may identify a possibility of one or more of viral infection, bacterial infection, gastroesophageal reflux disease (GERD), tonsillitis, cancer, etc. The AI throat analysis engine 312 may use AI to determine a state or condition. The AI throat analysis engine 312 may use AI to determine a range of possible states or conditions. The AI throat analysis engine 312 may associate a probability with each determined state or condition.

The AI heart analysis engine 314 may interpret audio of a heart taken by a sensor, such as the stethoscope 206 in FIG. 2. The AI heart analysis engine 314 may identify a possibility of one or more of heart murmurs, irregular heart rhythms, etc. The AI heart analysis engine 314 may use AI to determine a state or condition. The AI heart analysis engine 314 may use AI to determine a range of possible states or conditions. The AI heart analysis engine 314 may associate a probability with each determined state or condition.

The AI lung analysis engine 316 may interpret audio of a lung taken by a sensor, such as the stethoscope 206 in FIG. 2. The AI lung analysis engine 316 may identify a possibility of one or more of abnormal breathing sounds, wheezing, congestive sounds, etc. The AI lung analysis engine 316 may use AI to determine a state or condition. The AI lung analysis engine 316 may use AI to determine a range of possible states or conditions. The AI lung analysis engine 316 may associate a probability with each determined state or condition.

The AI arteriolar analysis engine 318 may interpret audio of one or more arteries (and/or the space between such) taken by a sensor, such as the stethoscope 206 in FIG. 2. The AI arteriolar analysis engine 318 may identify a possibility of one or more of arterial insufficiency, narrowing, blockage, etc. The AI arteriolar analysis engine 318 may use AI to determine a state or condition. The AI arteriolar analysis engine 318 may use AI to determine a range of possible states or conditions. The AI arteriolar analysis engine 318 may associate a probability with each determined state or condition.

The AI venous analysis engine 320 may interpret audio of one or more vessels (veins/venules and/or the space in between such vessels) taken by a sensor, such as the stethoscope 206 in FIG. 2. The AI venous analysis engine 320 may identify a possibility of one or more of venous insufficiency, narrowing, blockage, etc. The AI venous analysis engine 320 may use AI to determine a state or condition. The AI venous analysis engine 320 may use AI to determine a range of possible states or conditions. The AI venous analysis engine 320 may associate a probability with each determined state or condition.

The AI body temperature analysis engine 322 may interpret temperatures taken by a sensor, such as the IR thermometer 208 in FIG. 2. The AI venous analysis engine 320 may identify one of a normal temperature, a low grade fever, a significant fever, hypothermia, etc. The AI body temperature analysis engine 322 may use AI to determine a state or condition. The AI body temperature analysis engine 322 may use AI to determine a range of possible states or conditions. The AI body temperature analysis engine 322 may associate a probability with each determined state or condition.

The AI EKG analysis engine 324 may interpret EKG measurements taken by a sensor, such as the EKG 210 in FIG. 2. The AI EKG analysis engine 324 may identify a possibility of one or more of normal, arrhythmia, tachycardia, bradycardia, atrial fibrillation, missed beat, premature atrial contraction (PAC), premature ventricular contraction (PVC), ST elevation, ST depression, ventricular premature beat (VPB), accidental VPB, VPB trigeminy, VPB bigeminy, VPB couple, VPB runs of 3, VPB runs of 4, VPB RonT, etc. The AI EKG analysis engine 324 may use AI to determine a state or condition. The AI EKG analysis engine 324 may use AI to determine a range of possible states or conditions. The AI EKG analysis engine 324 may associate a probability with each determined state or condition.

The AI pulse oximeter analysis engine 326 may interpret pulse measurements and/or oxygen saturation levels taken by a sensor, such as the pulse oximeter 212 in FIG. 2. The AI pulse oximeter analysis engine 326 may identify a possibility of one or more of a fast pulse rate (e.g. heart, etc.), a slow pulse rate, a normal pulse rate, a normal oxygen saturation level, a low oxygen saturation level, etc. The AI pulse oximeter analysis engine 326 may use AI to determine a state or condition. The AI pulse oximeter analysis engine 326 may use AI to determine a range of possible states or conditions. The AI pulse oximeter analysis engine 326 may associate a probability with each determined state or condition.

The AI body fat and/or muscle tone sensor analysis engine 328 may interpret body fat and/or muscle tone measurements taken by a sensor, such as the body fat and/or muscle tone sensor 214 in FIG. 2. The AI body fat and/or muscle tone sensor analysis engine 328 may identify a possibility of one or more of obesity, wasting, etc. The AI body fat and/or muscle tone sensor analysis engine 328 may additionally use user-entered data, such as height and weight, to determine a fitness level. The AI body fat and/or muscle tone sensor analysis engine 328 may use AI to determine a state or condition. The AI body fat and/or muscle tone sensor analysis engine 328 may use AI to determine a range of possible states or conditions. The AI body fat and/or muscle tone sensor analysis engine 328 may associate a probability with each determined state or condition.

The AI glucose analysis engine 330 may interpret a concentration of glucose in a blood sample taken by a sensor, such as the glucometer 226 in FIG. 2. The AI glucose analysis engine 330 may identify a possibility of one or more of normal, prediabetes, diabetes, hypoglycemia, etc. The AI glucose analysis engine 330 may use AI to determine a state or condition. The AI glucose analysis engine 330 may use AI to determine a range of possible states or conditions. The AI glucose analysis engine 330 may associate a probability with each determined state or condition.

The AI hematology analysis engine 332 may interpret cells in a blood sample taken by a sensor, such as the hematology analyzer 228 in FIG. 2. The AI hematology analysis engine 332 may identify a possibility of one or more of sickle cell, anemia, human immunodeficiency virus (HIV), etc. The AI hematology analysis engine 332 may use AI to determine a state or condition. The AI hematology analysis engine 332 may use AI to determine a range of possible states or conditions. The AI hematology analysis engine 332 may associate a probability with each determined state or condition.

The AI feedback engine 334 may take as input health states and/or conditions determined by other modules. The AI feedback engine 334 may use the totality of health states and/or conditions to determine a diagnosis. The AI feedback engine 334 may use the totality of health states and/or conditions, or a trend of such over time, to determine a range of diagnoses. Each entry in the range of diagnoses may comprise an associated degree of certainty. The AI feedback engine 334 may assign an urgency level to each diagnosis. The AI feedback engine 334 may assign an urgency level associated with a most urgent entry in the range of diagnoses to the range of diagnoses. The AI feedback engine 334 may assign an urgency level associated with a most likely entry in the range of diagnoses to the range of diagnoses. The AI feedback engine 334 may assign a recommendation to each diagnosis. The AI feedback engine 334 may assign a recommendation associated with a most urgent entry in the range of diagnoses to the range of diagnoses. The AI feedback engine 334 may assign a recommendation associated with a most likely entry in the range of diagnoses to the range of diagnoses.

Processes for Remote and/or Automated Medical Diagnosis

Figure 4:
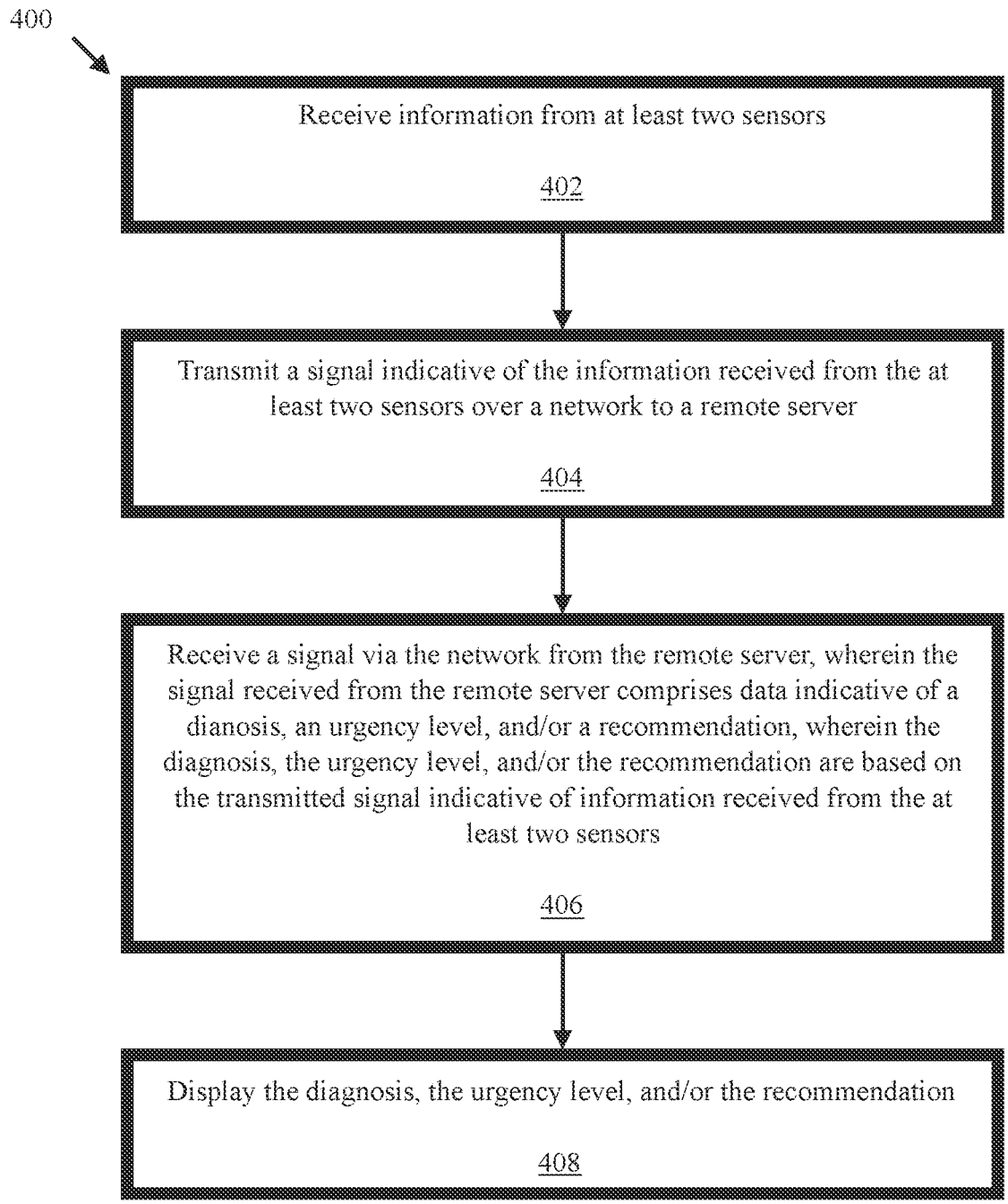
FIG. 4 illustrates a flowchart for remote and/or automated medical diagnosis in accordance with an exemplary embodiment of the invention.

FIG. 4 illustrates, in an example embodiment, method 400 of remote and/or automated medical diagnosis. In embodiments, the method steps or techniques depicted and described herein can be performed in a processor of the medical/consumer electronics device 140 in FIG. 1, the method steps being encoded as processor-executable instructions in a non-transitory memory of the medical/consumer electronics device 140. In embodiments, the method steps or techniques depicted and described herein can be performed in a processor the analysis system 120 in FIG. 1, the method steps being encoded as processor-executable instructions in a non-transitory memory of the telemedicine platform 120. The techniques of FIG. 4 may be implemented in an operating system kernel, in a separate user process, in a library package bound into network applications, on a specially constructed machine, on an application-specific integrated circuit (ASIC), or a field programmable gate array (FPGA).

At step 402, information may be received from at least two sensors. One of the at least two sensors may comprise and/or be associated with a high-magnification camera, a motorized camera, a stethoscope, an infrared (IR) thermometer, an electrocardiogram (EKG), a pulse oximeter, a body fat and/or muscle tone sensor, a glucometer, or a hematology analyzer. Information from the at least two sensors may comprise one or more of an eye image, a skin image, an ear image, a nose image, a throat image, chest sounds, a body temperature, EKG measurements, pulse measurements, an oxygen saturation level, a body fat measurement, a muscle tone measurement, a glucose measurement, and a hematology measurement.

At step 404, a signal indicative of the information received from the at least two sensors may be transmitted over a network to a remote server. The remote server may comprise a telemedicine platform. The remote server may comprise a cloud computing environment. The remote server may comprise an artificial intelligence (AI) system. The AI system may be trained on data from a data repository.

At step 406, a signal may be received via the network from the remote server. The signal received from the remote server may comprise data indicative of a diagnosis, an urgency level, and/or a recommendation. The diagnosis, the urgency level, and/or the recommendation may be based on the transmitted signal indicative of information received from the at least two sensors. The diagnosis, the urgency level, and/or the recommendation may be based on the AI system. The diagnosis may comprise a list of possible conditions. The list of possible conditions may be ordered by likelihood. The list of possible conditions may be ordered by severity. The urgency level may comprise a number within a range. The range may comprise, for example, 1 to 5. The low number may be the least urgent. The high number may be the least urgent. The recommendation may comprise initiating a call with a telemedicine physician. If multiple possible conditions are determined, then the urgency level associated with the most urgent condition of the possible conditions may be selected. If multiple possible conditions are determined, then the urgency level associated with the most likely condition of the possible conditions may be selected.

At step 408, the diagnosis, the urgency level, and/or the recommendation may be displayed. Items in the list of possible conditions that are associated with a threshold urgency and/or severity level may be displayed in a particular color and/or property. For example, possible conditions associated with an elevated severity or higher may be displayed in red and bold lettering. The urgency level may be displayed in a particular color and/or property if it is associated with a threshold urgency level. For example, if the urgency level is measured between 1 and 5 with 5 being the most urgent, then urgency levels at 4 or higher may be displayed in red and bold lettering. Recommendations associated with a threshold urgency and/or severity level may be displayed in a particular color and/or property. For example, recommendations associated with an elevated severity or higher may be displayed in red and bold lettering.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the embodiments disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific embodiments, at least some of the features or functionalities of the various embodiments disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some embodiments, at least some of the features or functionalities of the various embodiments disclosed herein may be implemented in one or more virtualized computing environments (e.g., network computing clouds, virtual machines hosted on one or more physical computing machines, or other appropriate virtual environments).

Figure 5:
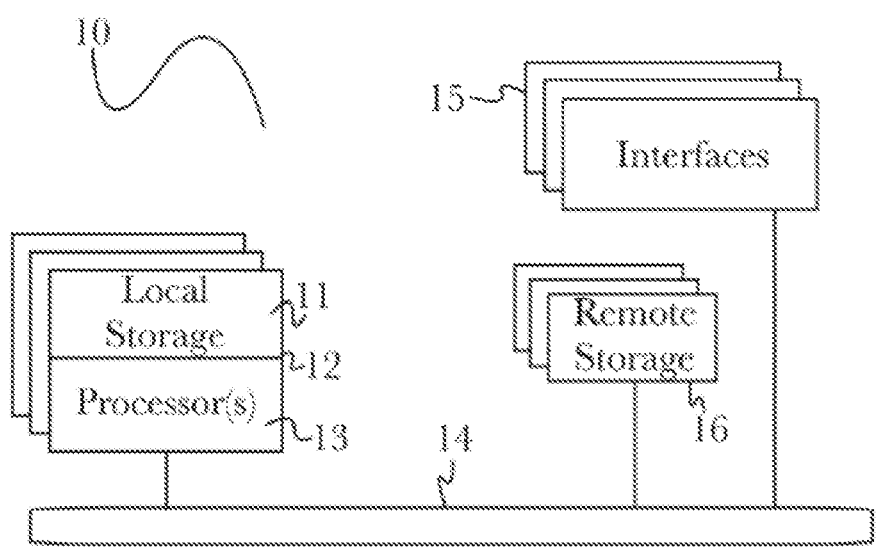
FIG. 5 illustrates components of an exemplary computing device that supports an embodiment of the inventive disclosure.

Referring now to FIG. 5, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some embodiments, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random-access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 5 illustrates one specific architecture for a computing device 10 for implementing one or more of the embodiments described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, single processor 13 handles communications as well as routing computations, while in other embodiments a separate dedicated communications processor may be provided. In various embodiments, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the embodiments described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

The medical/consumer electronics device 140 and/or the telemedicine platform 140 in FIG. 1 may be and/or comprise the computing device 10.

Because such information and program instructions may be employed to implement one or more systems or methods described herein, at least some network device embodiments may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 6:
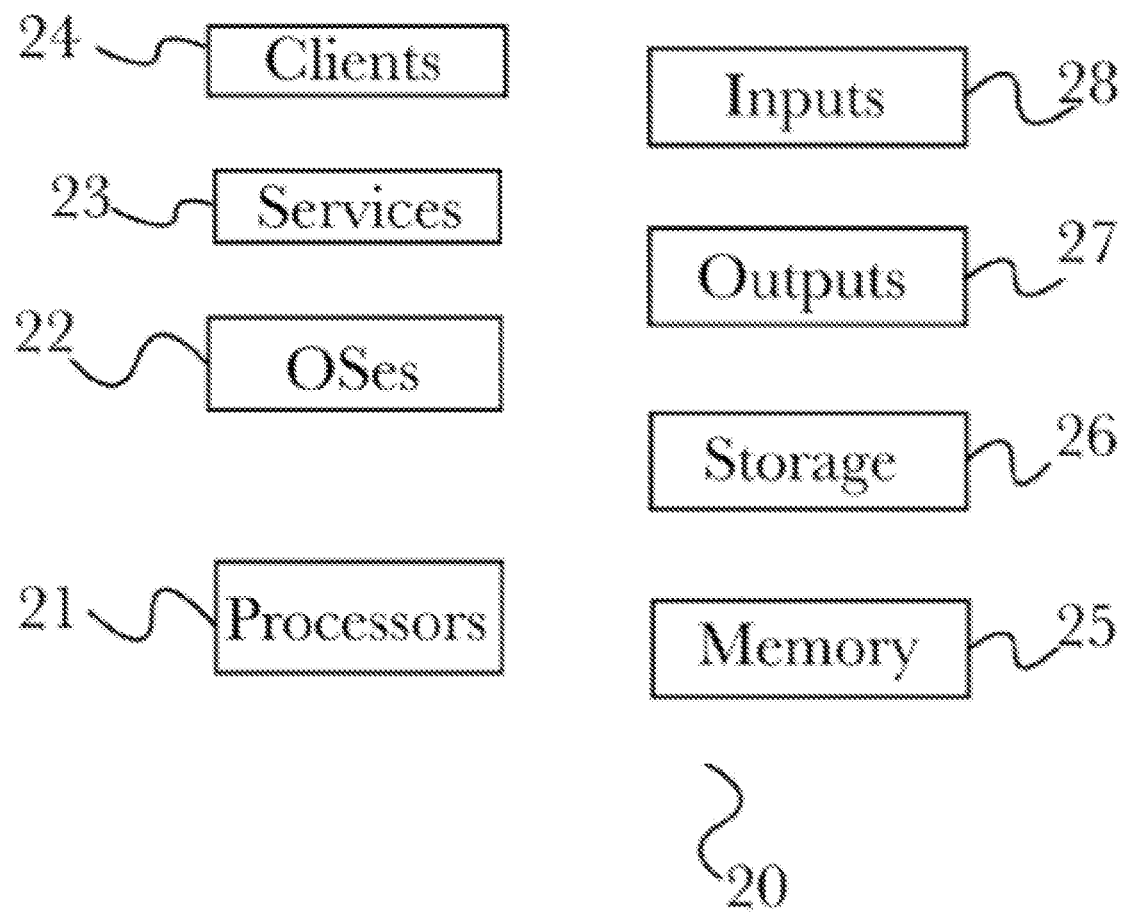
FIG. 6 illustrates one embodiment of a standalone computing system that supports an embodiment of the inventive disclosure.

In some embodiments, systems may be implemented on a standalone computing system. Referring now to FIG. 6 above, there is shown a block diagram depicting a typical exemplary architecture of one or more embodiments or components thereof on a standalone computing system. Computing device 20 includes processors 21 that may run software that carry out one or more functions or applications of embodiments, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 6). Examples of storage devices 26 include flash memory, magnetic hard drive, CD-ROM, and/or the like.

The medical/consumer electronics device 140 and/or the telemedicine platform 140 in FIG. 1 may be and/or comprise the system 20.

Figure 7:
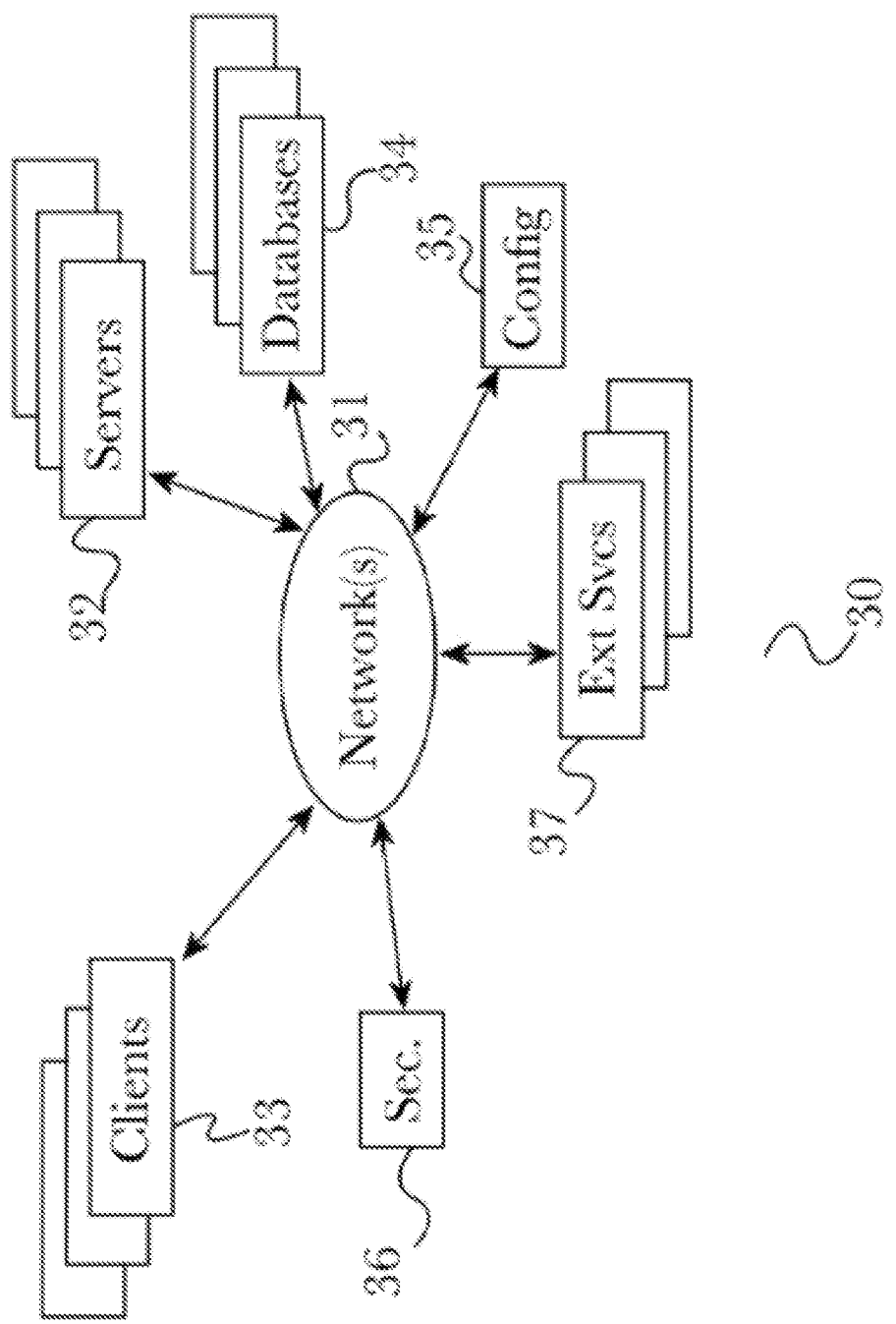
FIG. 7 illustrates an exemplary distributed computing network that supports an exemplary embodiment of the inventive disclosure.

In some embodiments, systems may be implemented on a distributed computing network, such as one having any number of clients and/or servers. Referring now to FIG. 7, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 6. In addition, any number of servers 32 may be provided for handling requests received from one or more clients 33. Clients 33 and servers 32 may communicate with one another via one or more electronic networks 31, which may be in various embodiments any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some embodiments, servers 32 may call external services 37 when needed to obtain additional information, or to refer to additional data concerning a particular call. Communications with external services 37 may take place, for example, via one or more networks 31. In various embodiments, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises.

In some embodiments, clients 33 or servers 32 (or both) may make use of one or more specialized services or appliances that may be deployed locally or remotely across one or more networks 31. For example, one or more databases 34 may be used or referred to by one or more embodiments. It should be understood by one having ordinary skill in the art that databases 34 may be arranged in a wide variety of architectures and using a wide variety of data access and manipulation means. For example, in various embodiments one or more databases 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some embodiments, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some embodiments may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with embodiments without limitation, unless a specific security 36 or configuration system 35 or approach is specifically required by the description of any specific aspect.

The medical/consumer electronics device 140 and/or the telemedicine platform 170 and/or the data repository 130 and/or the third party stakeholder platform 180 and/or the analysis system 120 in FIG. 1 may be and/or comprise the one or more of the server(s) 32.

Figure 8:
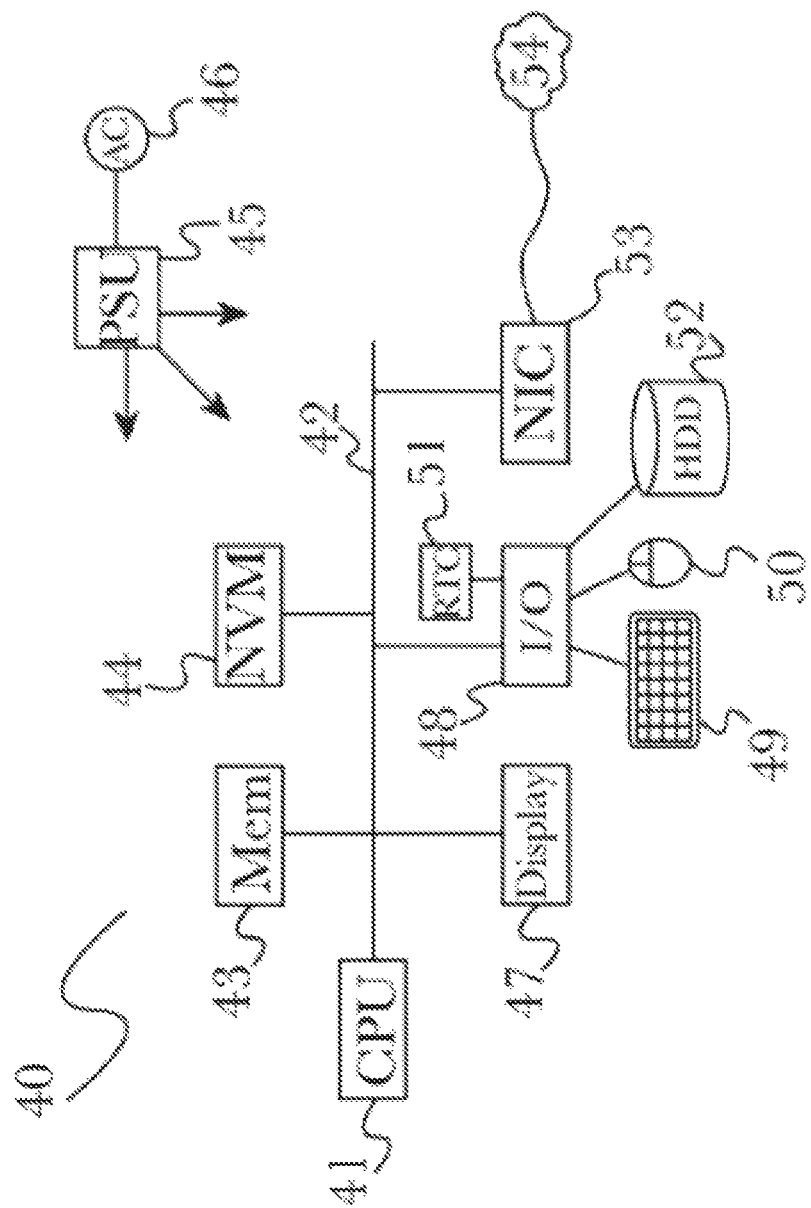
FIG. 8 illustrates an exemplary overview of a computer system that supports an exemplary embodiment of the inventive disclosure.

FIG. 8 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to keyboard 49, pointing device 50, hard disk 52, and real-time clock 51. NIC 53 connects to network 54, which may be the Internet or a local network, which local network may or may not have connections to the Internet. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

The medical/consumer electronics device 140 and/or the telemedicine platform 170 and/or the data repository 130 and/or the third party stakeholder platform 180 and/or the analysis system 120 in FIG. 1 may be and/or comprise the computer system 40.

In various embodiments, functionality for implementing systems or methods of various embodiments may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various embodiments described above. Accordingly, the present invention is defined by the claims and their equivalents.

Metaverse/Virtual World Telemedicine Integration

Figure 9:
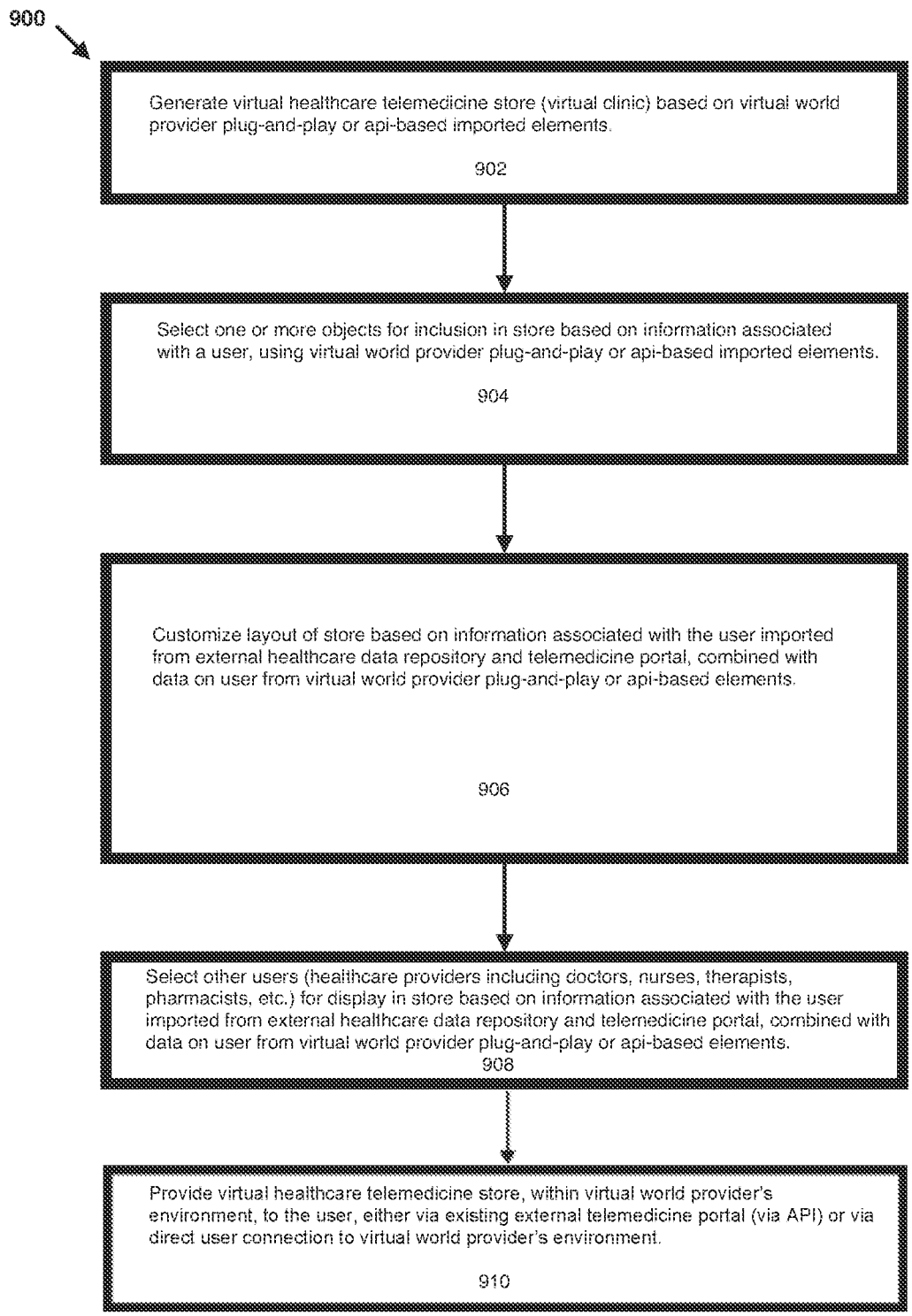
FIG. 9 illustrates a flowchart for remote and/or automated medical diagnosis and provision of care in accordance with an exemplary embodiment of the invention.

FIG. 9 illustrates, in an example embodiment, method 900 of remote and/or automated medical diagnosis and provision of care in a metaverse/virtual world. In embodiments, the method steps or techniques depicted and described herein can be performed in a virtual world/metaverse provider's environment, with possible assistance from/integration with one or more of the other systems, methods, and devices described in preceding sections and paragraphs of this disclosure.

At Step 902, a virtual healthcare telemedicine store (virtual clinic) is generated based on the virtual world provider's plug-and-play elements or API-based imported elements.

At Step 904, one or more objects for inclusion in the virtual store based on information associated with a user is selected, using the virtual world provider's plug-and-play or API-based imported elements.

At Step 906, a layout of the store based on information associated with the user imported from an external healthcare data repository (FIG. 1, 130) and telemedicine platform (FIG. 1, 170) is customized, combined with data on the user from the virtual world provider's plug-and-play or API-based elements.

At Step 908, other users (healthcare providers including doctors, nurses, therapists, pharmacists, etc.) are selected for display in the store based on information associated with the user imported from the external healthcare data repository (FIG. 1, 130) and telemedicine portal (FIG. 1, 170), combined with data on the user from the virtual world provider's plug-and-play or API-based elements.

At Step 910, a virtual healthcare telemedicine store is provided, within the virtual world provider's environment, to the user, either via the existing external telemedicine portal (FIG. 1, 170) (via API) or via direct user connection to the virtual world provider's environment.

The user may then interact with the virtual healthcare telemedicine store (within the virtual world provider's environment) in the same way s/he interacts with the pre-existing telemedicine application or website described in this disclosure, and may interact with the device(s) described in this disclosure and transmit data to (and receive data from) the virtual healthcare telemedicine store in conjunction with the pre-existing telemedicine application or website, the data repository, and all other network nodes and systems described in this disclosure.

FIG. 10 illustrates, in an example embodiment, of a process for computing blood pressure of an individual based on images of the eye of the individual. The exemplary process comprises receiving images of the outer eye of an individual 1001, computing a vessel measure for a blood vessel of the outer eye 1003, computing a blood pressure measure for the individual 1005, and providing a feedback result 1007.

At step 1001, the process may comprise receiving images of the outer eye of an individual. The images may be received from an end-user handheld electronics device (e.g. medical/consumer electronics device 140 or 200). The end-user handheld electronics device may comprise and/or interface with a high-magnification camera operable to capture digital images and/or video of the outer eye of an individual. The high-magnification camera may be integral with the end-user handheld electronics device. The high-magnification camera may be operable to capture digital images and/or video of blood flowing through the vasculature of the outer eye. The end-user handheld electronics device may be operable to capture and provide a sequence of digital images to a remote server for further processing. The sequence of images may comprise a series of time-stamped images. The images may be received in real-time as the images are acquired by the end-user handheld electronics device.

At step 1003, the process may comprise computing a vessel measure for at least one blood vessel present in the received images. Computing a vessel measure may comprise applying a computer vision algorithm, via a processor, to analyze the received images. The computer vision algorithm may extract pixel value information associated with at least one pixel for each image in the received images (e.g. each image of a sequence of images). The computer vision algorithm may analyze extracted pixel information to determine at least one image characteristic, including, but not limited to, blood vessel diameter, blood vessel wall thickness, blood vessel length, distance between blood vessels or vessel segments, area between blood vessels or vessel segments, and a blood velocity measurement associated with at least one blood vessel. The computed vessel measure may comprise one of the image characteristics. The computed vessel measure may comprise a measure computed from a combination of the image characteristics. The computed vessel measure may comprise a measure computed using at least one of the image characteristics. For example, the image characteristics may be used to compute at least one characteristic associated with blood flow through a vessel, including, but not limited to pressure, volume, resistance, volumetric flow rate, flow velocity, and cross sectional area associated with a blood vessel. The computer vision algorithm may determine at least one metric for the series of images including, but not limited to, at least one of a minimum blood vessel diameter, a maximum blood vessel diameter, an average blood vessel diameter, a minimum blood vessel wall thickness, a maximum blood vessel wall thickness, an average blood vessel wall thickness, an area between blood vessels (e.g. an area formed by surrounding blood vessels), a distance between blood vessels (e.g. a distance between the outer wall of a first blood vessel and the outer wall of a second blood vessel), a minimum blood velocity, a maximum blood velocity, and an average blood velocity. The computer vision algorithm may compute a vessel measure for at least one blood vessel based on the at least one metric for the series of images. In one aspect, blood flow characteristics may be computed based on the at least one image characteristic. In one aspect, changes in at least one of blood vessel diameter, blood vessel wall thickness, distance between blood vessels or vessel segments, and area between blood vessels or vessel segments, may indicate a change in blood flow characteristics. For example, an increase in blood vessel diameter may be associated with an change in blood flow characteristics (e.g. decreased pressure, increased volume, and/or decreased velocity), while a decrease in blood vessel diameter may be associated with an opposite change in flow characteristics (e.g. increased pressure, decreased volume, and/or increased velocity. Similarly, a decrease in the space between blood vessels (e.g. distance, area, etc.) may indicate an increase in blood vessel diameter of the blood vessels associated with that space due to increased flow (e.g. decreased pressure, increased volume, and/or decreased velocity). In other words, a decrease in the space between blood vessels may indicate an increase in flow characteristics, while an increase in the space between blood vessels may indicate a decrease in flow characteristics.

The computer vision algorithm may comprise a pre-processing step or algorithm(s) operable to prepare the images for further analysis. Pre-processing may include, but is not limited to, noise reduction, filtering, smoothing, contrast enhancement, artifact removal, scaling, dilation, erosion, etc. The computer vision algorithm may comprise at least one of object detection, edge detection, video tracking, object recognition, 3D pose estimation, and motion estimation (e.g. tracking and/or optical flow). The computer vision algorithm may comprise windowing such that selective processing is performed on pixels meeting certain value criteria (e.g. a minimum value threshold, a maximum value threshold). The computer vision algorithm may comprise area of interest or region of interest analysis, such that selective processing is performed on pixels within a specified location within the image (e.g. locations where blood vessels are identified). The computer vision algorithm may determine velocity by tracking at least one pixel within a specified region of interest. The region of interest may be of a specified size. The region of interest may be a fixed size. The region of interest may be smaller than the total size of an image being analyzed. The region of interest may be at a fixed location across a sequence of images.

The computer vision algorithm may be trained using machine learning techniques such as neural networks and/or deep learning. The computer vision algorithm may be trained using at least one of supervised learning, unsupervised learning, semi-supervised learning, and reinforcement learning. The computer vision algorithm may be trained using at least one of linear regression, logistic regression, decision trees, random forest algorithm, support vector machines, Naive Bayes algorithm, random walk algorithm, k-nearest neighbor algorithm, k-means clustering, and Markov models. These training approaches are merely exemplary and other training approaches/techniques may be used without departing from the scope of the invention as would be apparent to one of ordinary skill in the art. The computer vision may be trained using labeled images. The labeled images may comprise labels (e.g. labeled pixels) for at least one of a blood vessel, blood vessel wall, blood flow region, inner blood vessel diameter, outer blood vessel diameter, distance between blood vessels or vessel segments, area between blood vessels or vessel segments, and blood velocity.

At step 1005, the process may comprise computing a blood pressure measure for an individual based on obtained images of the outer eye of the individual. Computing a blood pressure measure may comprise computing, by a processor, a blood pressure measure using an artificial intelligence (AI) analysis algorithm. The AI analysis algorithm may relate at least one image characteristic and/or a computed vessel measure (e.g. as determined by the computer vision algorithm) to blood pressure values. The AI analysis algorithm may be trained using machine learning techniques such as neural networks and/or deep learning. The AI analysis algorithm may be trained using at least one of supervised learning, unsupervised learning, semi-supervised learning, and reinforcement learning. The AI analysis algorithm may be trained using at least one of linear regression, logistic regression, decision trees, random forest algorithm, support vector machines, Naive Bayes algorithm, random walk algorithm, k-nearest neighbor algorithm, k-means clustering, and Markov models. These training approaches are merely exemplary and other training approaches/techniques may be used without departing from the scope of the invention as would be apparent to one of ordinary skill in the art.

The AI analysis algorithm may be trained using previously acquired images of the outer eye vasculature of the individual and/or previously obtained blood pressure measurements associated with the individual. The previously acquired images may have been processed using the computer vision algorithm as described above. The AI analysis algorithm may be trained using previously acquired and processed images of the outer eye of the individual obtained in combination (e.g. simultaneously) with previously obtained blood pressure measurements associated with the individual. The previously acquired images and previously acquired blood pressure measurement may be obtained in combination with each other (e.g. simultaneously) at a plurality of different timepoints (e.g. multiple time points over the course of a day and/or several days or weeks). For example, for each user or individual being examined/imaged using the end-use handheld electronics device, corresponding outer eye vasculature imaging and blood pressure measures may be repeated over time for use in training an AI analysis algorithm. In one aspect, the AI analysis algorithm may rely on a generalized model trained using broader population data (e.g. a combination of images and blood pressure measures for a plurality of different individuals) in computing blood pressure measures. In one aspect, the corresponding imaging and blood pressure measures acquired for each user or individual are used to train an AI analysis algorithm unique to the user or individual. Because each individual may have different outer eye vasculature characteristics which may correspond to different blood pressure measures as compared to other individuals, an AI analysis algorithm unique to each individual may allow for a more accurate blood pressure measurement than a generalized model which attempts to compute blood pressure using a model trained using broader population data.

The AI analysis algorithm may compute an amount of change in at least one image characteristic (e.g. as determined by the computer vision algorithm). The AI analysis algorithm may compute the amount of change by comparing at least one current image characteristic with at least one previously computed image characteristic associated with the individual (e.g. from images previously acquired on a different day and/or time, such as baseline images and/or images used in training). The AI analysis may compute a percentage change in at least one image characteristic. The AI analysis algorithm may compute the blood pressure measure based on the amount of change. The AI analysis algorithm may compute blood pressure based on magnitude of change such that the computed blood pressure increases or decreases by an amount relative to the magnitude of change. The AI analysis algorithm may compute blood pressure based on the direction of change such that the computed blood pressure increases or decreases in relation to whether the computed change is an increase or decrease. The AI analysis algorithm may compute an amount of change in the space between blood vessels between a current image(s) and previously acquired image(s). The change in space between blood vessels may serve as an indicator of vessel diameter change which can be an indicator of blood flow changes (e.g. pressure, volume, velocity, etc.). For example, a decrease in the space between blood vessels between previous images and current images may indicate a lower blood pressure at the current time as compared to the previous time due to expansion of the blood vessel diameter which thereby reduced the computed space between blood vessels. Although described herein as separate algorithms, the computer vision algorithm and AI analysis algorithm could be combined into a single algorithm performing the combined functions of each individual algorithm without departing from the scope of the invention. Similarly, each algorithm could be further broken down into smaller or sub-algorithms which collectively perform the same fundamental functions without departing from the scope of the invention.

At step 1007, the process may comprise providing a feedback result to the handheld end-user electronics device. The feedback result may be provided via network communication. The feedback result may comprise at least the computed blood pressure. The feedback result may comprise at least one of the above computed metrics including, but not limited to, computed blood pressure, blood vessel diameter, blood vessel wall thickness, blood vessel length, distance between blood vessels or vessel segments, area between blood vessels or vessel segments, a blood velocity measurement associated with at least one blood vessel, and computed change metrics. Providing a feedback result may comprise providing a feedback result in near real-time, such that upon receiving images from a handheld end-user device, the images are processed according to the above and upon completion of processing the feedback result is promptly provided to the end-user electronics device for display. The feedback result may be at least one of prepared in a format and converted to a format transmissible over a network. The feedback result may be prepared in a format and/or communicated in a format suitable for display on the handheld end-user electronics device.

FIG. 11A illustrates an exemplary medical electronics device 140 for gathering and analyzing biometric information. The device 140 may comprise camera 1101, a high magnification camera 1103, an AI interface 1105, an AI processing module 1107, an authorization module 1109, a display 1111, a controller 1113, and a power source 1115.

The camera 1101 may comprise a device capable of capturing images of an eye of an individual. The camera 1101 may transmit the image(s) to a controller 1113. The camera 1101 may be a digital capture device that is capable of capturing 1080p resolution or higher. The camera 1101 may be capable of capturing an image of at least a portion of an eye in detail. The camera 1101 may be capable of capturing an image of the structures of the outer eye including at least the blood vessels and scleral tissue. Camera 1101 may comprise a visible light camera (e.g. an RGB camera). The camera 1101 may comprise an image sensor, including but not limited to at least one of a CMOS sensor, reflective mirror sensor, and CCD sensor. The image may be captured in various file formats, including JPEG for compressed, widely compatible photos, RAW for high-quality, unprocessed images, and TIFF for lossless, high-resolution files. The camera 1101 may also be a device capable of importing images of the same resolution which may include, but is not limited to a scanner or a data reading device.

The high magnification camera 1103 may comprise a device capable of capturing images of an eye of a user. The high magnification camera 1103 may transmit the image(s) to a controller 1113. The high magnification camera 1103 may be operable to capture images at a magnification greater than that of camera 1101. The high magnification camera 1103 may be a digital capture device that has a resolution higher than the camera 1101. In an embodiment of the invention, the high magnification camera 1103 may have magnification capability of 5×, 10×, 50×, 500×, 1000×. These are merely exemplary and any magnification camera capable of capturing blood flow could be used. The high magnification camera 1103 may comprise an image sensor, including but not limited to at least one of a CMOS sensor, reflective mirror sensor, and CCD sensor. Single lens, multi-lens, software/hardware based magnification. The high magnification camera 1103 may be capable of capturing a series of images at a frequency such that the blood flow in an eye can be observed. High magnification camera 1103 may comprise a visible light camera (e.g. an RGB camera). The image may be captured in various file formats, including JPEG for compressed, widely compatible photos, RAW for high-quality, unprocessed images, and TIFF for lossless, high-resolution files. The camera 1103 may also be a device capable of importing images of the same resolution which may include, but is not limited to a scanner or a data reading device.

The artificial intelligence (AI) interface 1105 may comprise a set of components capable of transmitting the information captured from the cameras 1101 and 1103 to an artificial intelligence processing module. The AI interface 1105 may receive input from an AI processing module such as AI inferences or other output resulting from AI processing of the images. The AI interface 1105 may include a set of wires for transmitting data, or a wireless transmitter, which may include, but is not limited to Wi-Fi, Bluetooth, and cellular networks. The AI interface in an alternative embodiment, may be omitted in favor of storing the AI onto the medical electronics device 140.

The artificial intelligence (AI) processing module 1107 may comprise a computer readable medium comprising code or computer readable instructions for executing a series of steps for analyzing the images captured by the cameras 1101 and 1103. The AI processing module 1107 may comprise either a database or a component for connection to a remote database which contains identity information about users. Although depicted as part of the medical electronics device 140, the AI processing module 1107 may be located external to or remote from medical electronics device 140 in which case the AI interface 1105 serves as the communication interface between medical electronics device 140 and AI processing module 1107. The AI processing module 1107 may determine at least one pattern characteristic of the vasculature from the first image captured by the camera 1101. This pattern characteristic recognition may be executed by at least one of convolutional neural networks (CNNs) for deep learning, and image segmentation algorithms for precise region identification. The AI processing module 1107 may determine at least one blood flow characteristic from the series of second images. Determining blood flow characteristic may comprise comparison of a plurality of images captured from the high magnification camera 1103. The analysis may comprise comparing the image of vasculature within the eye to see the blood flow and providing a blood flow analysis. The steps may further comprise comparing the at least one pattern characteristic and the at least one blood flow characteristic with a database of previously established pattern characteristics and blood flow characteristics for a plurality of individuals. The comparison may provide at least one indication of a match to an individual and a confidence in the level of match. AI processing module 1107 may verify the identity of a user based on the match. The AI processing module 1107 may use a set of thresholding rules to compare the image characteristics (pattern and blood flow) with the known characteristics of users in the database. The database may be remotely connected to the device 140 or contained on the device 140. Other image analysis techniques known in the art may be utilized to form both the vasculature pattern and the blood flow analysis.

The authorization module 1109 may comprise a computer readable medium that comprises code or computer readable instructions for determining authorizations based on the identity information determined by AI processing module 1107. The authorization module 1109 may compare an identified user with a set of permissions for the identified user. This may determine if a user has permission to access at least one of an area, a device, and information. In one aspect, the authorization check may be performed in response to an access request prompting the above described image acquisition and processing. If the identified user has appropriate permissions as determined by the authorization module 1109, access may be provided and if insufficient permissions are present, access will be denied. Alternatively, if the user identity can not be determined from the analysis, access will be denied and the user will be notified that the user identity could not be determined.

The display 1111 may comprise a screen in communication with the controller 1113. The screen may comprise at least one of a black and white screen, a color screen, a light, or other indicator means known in the art. The screen is capable of displaying the results of the analysis performed by at least one of the AI processing module 1107 and authorization module 1109. For example, the display 1111 may display at least one of a determined identity of an individual resulting from analysis of the obtained images (e.g. displaying an individual's name, likeness (e.g. a picture of the individual), and/or other identifying information). The display may display at least one indicator of the authorization status of the user (e.g. whether access is granted or denied, the level of access of the user being granted, the level of access needed for the user to gain the requested access, etc.). The screen may be located on the device or in an alternative embodiment of the invention it may be located remotely from the device.

The controller 1113 may comprise a microprocessor, computer and/or control circuitry capable of interfacing with the cameras 1101 and 1103, the AI interface 1105, the AI processing module 1107, the authorization module 1109 and the display 1111. The controller may comprise a user interface capable of receiving input and providing an indication of the instructions sent to the device 140.

The power source 1115 may provide the energy to operate the device 140. The power source 1115 may comprise a battery or may be hardwired for connection to an external power supply (e.g. an outlet, power grid, etc.).

FIG. 11B illustrates an exemplary AI processing module 1107 for analyzing obtained images (e.g. those obtained via a medical electronics device 140). The AI processing module 1107 may comprise data input interface 1121, a pattern analysis engine 1123, a blood flow analysis engine 1125, a database interface 1127, an identity engine 1129, and a data output interface 1131.

The data input interface 1121 may comprise at least one of computer readable instruction and a device for importing images into the AI processing module 1107. This interface may include physical connections, such as a direct connection to the cameras 1101 and 1103, USB and memory card slots. Wireless methods comprising at least one of Wi-Fi and Bluetooth may enable image import without the use of a physical connection. Alternatively, cloud-based services can be accessed by the data input interface 1121. File types may comprise, but are not limited to, JPEG for compressed, widely compatible photos, RAW for high-quality, unprocessed images, and TIFF for lossless, high-resolution files. The data input interface 1121 may standardize the input images into a universal format.

The pattern analysis engine 1123 may comprise a computer readable medium comprising code or computer readable instructions operable to execute a series of steps that is capable of analyzing a single image to detect patterns within the image. In an embodiment of the invention, the images comprise images of an eye, in particular the outer eye and corresponding scleral vasculature. Pattern analysis engine 1123 may apply image pre-processing to address common image quality issues such as blur, noise, etc. Pattern analysis engine 1123 may apply pre-processing to prepare the images for further analysis such as contrast enhancement in the image to make the vessels more prominent. These images may go through edge detection to highlight the blood vessels present. Once the blood vessels are clear in the image, and noise has been reduced, the width of the blood vessels may be skeletonized to simplify the pattern present. The bifurcation and crossover points may be identified as well. These steps would then create an eye pattern that can be compared to those in a database. In one aspect, the pattern of the vasculature may be used as the identified pattern for comparison purposes. In one aspect, the pattern of the sclera around blood vessels may be used as the identified pattern for comparison purposes.

The blood flow analysis engine 1125 may comprise a computer readable medium comprising code or computer readable instructions operable to execute a series of steps that is capable of analyzing multiple high definition images to create at least one of a blood flow diagram and a blood flow metric. The blood flow analysis engine 1125 may analyze blood flow (e.g. velocity) in the same manner as discussed above with respect to FIG. 10. The blood flow analysis engine may comprise the steps of reducing noise by using temporal and spatial filters in the sequence of images. The blood flow analysis engine 1125 may also comprise steps to align the sequence of images to account for any slight movements of the eye during capture. The blood flow analysis engine 1125 may then compute the motion vector of each pixel between frames. Techniques like the Lucas-Kanade method or Horn-Schunck method can be applied to detect and visualize blood flow. The blood flow analysis engine 1125 may then compute the flow velocity by analyzing the displacement of blood over time or by other known methods in the art. Similarly, the blood flow analysis engine 1125 may compute the flow direction in each vessel. The blood flow analysis engine 1125 may use the width and speed of blood vessels, approximate the volume of blood flow. The blood flow analysis engine 1125 may also perform pulse wave analysis to observe the pulsatile nature of blood flow, which could be influenced by heartbeats, to extract unique features.

The database interface 1127 is operable to interface with a database of previously acquired images and/or image processing results for a plurality of different individuals. The database interface 1127 is operable to obtain data from the database for comparison with the current images being analyzed such as for matching analysis of the currently identified pattern and blood flow characteristics with pattern and blood flow characteristics stored in the database. The database interface 1127 may be used to periodically update the database with new images or image characteristics (e.g. adding new individuals to the database) and/or to refine or replace older entries.

The identity engine 1129 may comprise a computer readable medium comprising code or computer readable instructions operable to execute a series of steps that is capable of analyzing the processed images from the pattern analysis engine 1123 and the blood flow analysis engine 1125 to match to the data extracted from the database interface 1127 to identify the user. The steps may comprise matching the image to a template of similar images to speed up the matching step. The templates may be stored on the device 140 or on a database 130. Dynamic templates may be employed in an embodiment of the invention. Dynamic templates may capture the essence of an individual's blood flow patterns over time. Matching the blood flow may comprise a step of feature vector comparison by creating a feature vector for each image, then measuring the similarity of the new image's feature vector to those in the database using cosine similarity. As the steps are repeated, the AI processing module 1107 may be improved through machine learning to classify or identify individuals based on the extracted features. The steps may also be improved through at least one of hashing techniques to reduce the dimensionality of feature vectors and speed up the search and nearest neighbor search to find the closest match in the database.

The data output interface 1131 may comprise a device to connect the AI processing module 1107 to the device 140. The interface 1131 may provide encryption steps to provide anonymity to a user and the data within the database.

FIG. 12 illustrates a method of gathering and analyzing biometric information. The method may comprise the steps of obtain a first image of the outer eye of an individual 1201, obtain a series of second images of the outer eye of the individual 1203, determine a pattern characteristic based on the first image 1205, determine a blood flow characteristic based on the second images 1207, determine identity of the individual 1209, providing a feedback result 1211

Obtain a first image of the outer eye of an individual 1201 may comprise using a first image capture device to take an image of the user's eye. In an embodiment of the invention a single image is obtained, but multiple images could be used for improving the reliability of the analysis. Alternatively, the image or plurality of images may be obtained from other digital readable media. The first image generally comprises the structures of the outer eye including at least blood vessels and scleral tissue.

Obtain a series of second images of the outer eye of the individual 1203 may comprise using a high resolution image capture device capable of imaging blood flow within the blood vessels of an eye to capture a series of images over time. The images may be labeled in the order they were obtained in order to show the flow direction of blood within the vessels of the eye. Alternatively, these images may be obtained from other digital readable media. Alternatively, the high resolution image capture device may be the same device as the first image capture device.

Determine a pattern characteristic based on the first image 1205 may comprise analyzing the image from the first image capture device. The determination 1205 may comprise reducing noise in the image through image processing techniques known in the art. In addition, the determination of a pattern characteristic 1205 may comprise enhancing the contrast within the obtained image(s) to further highlight the blood vessels. The determination of a pattern characteristic 1205 may comprise skeletonizing the blood vessels and highlighting the bifurcation and crossover points in the blood vessels. At the end of determination of a pattern characteristic 1205 a pattern is generated for comparison with other patterns within a database of known individual patterns.

Determine a blood flow characteristic based on the second images 1207 may comprise analyzing the images from the high resolution image capture device. The blood flow characteristic analysis 1207 may comprise the steps of reducing noise by using temporal and spatial filters in the sequence of images. The blood flow characteristic analysis 1207 may also comprise steps to align the sequence of images to account for any slight movements of the eye during capture. The blood flow characteristic analysis 1207 may then compute the motion vector of each pixel between frames. Techniques like the Lucas-Kanade method or Horn-Schunck method can be applied to detect and visualize blood flow. The blood flow characteristic analysis 1207 may then compute the flow velocity by analyzing the displacement of blood over time or by other known methods in the art. Similarly, the blood flow characteristic analysis 1207 may compute the flow direction in each vessel. The blood flow characteristic analysis 1207 may use the width and speed of blood vessels, approximate the volume of blood flow. The blood flow characteristic analysis 1207 may also perform pulse wave analysis to observe the pulsatile nature of blood flow, which could be influenced by heartbeats, to extract unique features.

Determine identity of the individual 1209 may comprise comparing the analysis from the pattern characteristic 1205 and blood flow characteristic analysis 1207 to the known patterns and blood flow characteristics. Determine identity of the individual 1209 may involve using static and dynamic templates to speed up the matching process. The steps may be improved over time by utilizing machine learning to improve the accuracy of the matching process.

Providing a feedback result 1211 may comprise at least one of providing a message or indication or providing access of a locked or restricted area or data. The result may be provided through at least one of a display and indicator known in the art. Inconclusive results from the step of determine identity of the individual 1209 may provide a separate indication for a user encouraging them to provide new images.

ADDITIONAL CONSIDERATIONS

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for remote and/or automated medical diagnosis through the disclosed principles herein. Thus, while particular embodiments and applications have been illustrated and described, it is to be understood that the disclosed embodiments are not limited to the precise construction and components disclosed herein. Various apparent modifications, changes and variations may be made in the arrangement, operation and details of the method and apparatus disclosed herein without departing from the spirit and scope defined in the appended claims.

What is claimed is:

1. A computer implemented method for artificial intelligence (AI) enabled biometric identification of individuals, the computer implemented method comprising:
   controlling a first visible light camera to obtain a first image of at least a portion of the vasculature of the scleral tissue of the outer eye of an individual;
   controlling a second visible light camera to obtain a series of second images of the vasculature of the scleral tissue of the outer eye, the second images obtained at a higher magnification than the first image, the series of second images capturing blood flow through at least one blood vessel segment of the scleral tissue of the outer eye of the individual;
   transmitting the first image and series of second images to an AI processing module;
   receiving from the AI processing module, identity information associated with the individual, wherein the AI processing module employs at least one machine learning algorithm trained on pattern and flow characteristics of the vasculature of the scleral tissue of the outer eye, wherein the identity information is determined by the AI processing module by:
   a) determining at least one pattern characteristic of the vasculature from the first image;
   b) determining at least one blood flow characteristic from the series of second images;
   c) comparing the at least one pattern characteristic and the at least one blood flow characteristic with a database of previously established pattern characteristics and blood flow characteristics for a plurality of individuals;
   d) determining identity information for the individual when the comparison results in a match exceeding a match threshold; and
   providing an authorization indication based on the identity information, the authorization indication granting or denying the user access to at least one of a location, a device, and information.

2. The computer implemented method according to claim 1, wherein the AI processing module is located within a housing associated with the first and second cameras or located remote from a housing associated with the first and second cameras.

3. The computer implemented method according to claim 1, wherein granting access to a location comprises allowing the individual access to a secured area.

4. The computer implemented method according to claim 1, wherein granting access to a device comprises unlocking a device thereby allowing the individual to interact with operational aspects of the device.

5. The computer implemented method according to claim 1, wherein granting access to information comprises displaying targeted advertisement information to the individual based on the identity information.

6. The computer implemented method according to claim 1, further comprising displaying at least one of the identity information associated with the individual and the authorization indication.

7. The computer implemented method according to claim 1, wherein the first image is obtained during a time when the series of second images are obtained.

8. The computer implemented method according to claim 1, wherein the pattern characteristics comprising blood vessel patterns are associated with at least one of blood vessel distribution and blood vessel branching.

9. The computer implemented method according to claim 1, wherein the pattern characteristics comprising patterns of space between blood vessels associated with a shape and/or size of non-blood vessel areas of the outer eye.

10. The computer implemented method according to claim 1, wherein the at least one blood flow characteristic comprising at least one of blood flow velocity, maximum blood vessel diameter, and minimum blood vessel diameter.

11. The computer implemented method according to claim 10, wherein the at least one blood flow characteristic is determined by determining a pixel velocity across a plurality of images of the series of second images.

12. A computer implemented method for artificial intelligence (AI) enabled biometric identification of individuals, the computer implemented method comprising:
   obtaining a first image of at least a portion of the vasculature of the scleral tissue of the outer eye of an individual, the first image obtained from a first camera;
   obtaining a series of second images of the vasculature of the scleral tissue of the outer eye of the individual, the series of second images obtained from a second camera, wherein the series of second images are obtained at a higher magnification than the first image;
   applying a first AI algorithm to analyze the first image from the first camera to determine at least one pattern characteristic associated with the eye vasculature;
   applying a second AI algorithm to analyze the images from the second camera to determine at least one blood flow characteristic within the eye vasculature;
   applying a third AI algorithm to determine an identity of the individual based on the at least one pattern characteristic and the at least one blood flow characteristic, the third AI algorithm operable to compare the at least one pattern characteristic and the at least one blood flow characteristic with a database of previously established pattern characteristics and blood flow characteristics for a plurality of individuals.

13. A system for artificial intelligence (AI) enabled biometric identification of individuals, the system comprising:
   a housing;
   a first camera;
   a second camera, the second camera comprising a high magnification camera;
   control circuitry comprising at least one processor operable to:
      control the first camera to obtain a first image of the vasculature of the outer eye of an individual;
      control the second camera to obtain a series of second images of the vasculature of the outer eye, the second images obtained at a higher magnification than the first image, the series of second images capturing blood flow through at least one blood vessel segment of the outer eye of the individual;
   an AI interface engine, the AI interface engine comprising at least one processor operable to:
   transmit the first image and series of second images to an AI processing module;
   receive from the AI processing module, identity information associated with the individual, wherein the AI processing module employs at least one machine learning algorithm trained on pattern and flow characteristics of the vasculature of the scleral tissue of the outer eye.

14. The system according to claim 13, wherein the AI interface engine is integrated into the system.

15. The system according to claim 13, wherein the AI interface engine is communicatively coupled via at least one of a network interface and electronic communication interface with an AI processing module that is located in a remote server.

* * * * *